United States Patent [19]

Saedi et al.

[11] Patent Number: 6,103,237
[45] Date of Patent: Aug. 15, 2000

[54] STABLE VARIANT HK2 POLYPEPTIDE

[75] Inventors: Mohammad Saeed Saedi; Stephen Dennis Mikolajczyk; Abhay Kumar; Kristine Kuus-Reichel, all of San Diego, Calif.

[73] Assignee: Hybritech Incorporated, San Diego, Calif.

[21] Appl. No.: 08/622,046

[22] Filed: Mar. 26, 1996

Related U.S. Application Data

[63] Continuation-in-part of application No. 08/427,767, May 2, 1995, abandoned, which is a continuation-in-part of application No. 08/241,174, May 10, 1994, abandoned, which is a continuation-in-part of application No. 08/096,946, Jul. 22, 1993, Pat. No. 5,516,639.

[51] Int. Cl.$^7$ .......................... A61K 39/00; A61K 38/00; C07K 1/00

[52] U.S. Cl. ...................... 424/185.1; 530/324; 530/350

[58] Field of Search ............................... 435/69.1, 185.1, 435/7.23, 7.4, 7.9; 530/350, 324; 424/185.1

[56] References Cited

U.S. PATENT DOCUMENTS

| | | | |
|---|---|---|---|
| 3,817,837 | 6/1974 | Rubenstein et al. | 195/103 |
| 3,842,067 | 10/1974 | Sarantakis | 260/112 |
| 3,850,752 | 11/1974 | Schuurs et al. | 195/103 |
| 3,862,925 | 1/1975 | Sarantakis et al. | 260/112 |
| 3,901,654 | 8/1975 | Gross | 23/230 |
| 3,935,074 | 1/1976 | Rubenstein et al. | 195/103 |
| 3,972,859 | 8/1976 | Fujino et al. | 260/112 |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,092,408 | 5/1978 | Litt | 436/531 |
| 4,098,876 | 7/1978 | Piasio et al. | 424/1 |
| 4,105,602 | 8/1978 | Colescott et al. | 260/8 |
| 4,353,982 | 10/1982 | Gomez et al. | 435/7 |
| 4,371,515 | 2/1983 | Chu | 436/544 |
| 4,446,122 | 5/1984 | Chu et al. | 424/1 |
| 4,487,715 | 12/1984 | Nitecki et al. | 260/112 |
| 4,629,783 | 12/1986 | Cosand et al. | 530/324 |
| 4,757,048 | 7/1988 | Lewicki et al. | 514/11 |
| 4,792,528 | 12/1988 | Canfield et al. | 436/515 |
| 5,516,639 | 5/1996 | Tindall et al. | 435/7.4 |

FOREIGN PATENT DOCUMENTS

| | | | |
|---|---|---|---|
| 0 228 243 A1 | 7/1987 | European Pat. Off. | G01N 33/577 |
| 0297913 | 1/1989 | European Pat. Off. | C12N 15/00 |
| 0 571 911 A2 | 12/1993 | European Pat. Off. | C12Q 1/68 |
| 94/10343 | 5/1994 | WIPO | C12Q 1/68 |
| 95/03334 | 2/1995 | WIPO | C07K 16/40 |
| WO 95/03334 | 2/1995 | WIPO | . |
| 95/28498 | 10/1995 | WIPO | C12Q 1/68 |
| 95/30758 | 11/1995 | WIPO | C12N 15/57 |
| 96/21042 | 7/1996 | WIPO | C12Q 1/68 |
| 96/26272 | 8/1996 | WIPO | C12N 15/12 |
| 96/26442 | 8/1996 | WIPO | C01N 33/574 |
| 96/34964 | 11/1996 | WIPO | C12N 15/57 |
| 97/01630 | 1/1997 | WIPO | C12N 9/64 |

OTHER PUBLICATIONS

P. Altman, et al., "Inbred and Genetically Defined Strains of Laboratory Animals", *Biological Handbooks, III, Federation of American Societies for Experimental Biology*, pp. 21 and 29.

P. Andrews, et al., "Tumor–promoting Phorbol Ester Down–Regulates the Androgen Induction of Prostate–specific Antigen in a Human Prostatic Adenocarcinoma Cell Line," *Cancer Research*, 52, 1525–1529 (Mar., 1992).

A. Angermann, et al., "Purification and characterization of human salivary–gland prokallikrein from recombinant baculovirus–infected insect cells", *Eur. J. Biochem.*, 206, 225–233 (1992).

A. Baker, et al., "Human Kidnay Kallikrein: cDNA Cloning and Sequence Analysis", *DNA*, 4, 445–450 (1985).

T. Berg, et al., "A Common Nomenclature for Members of the Tissue (Glandular) Kallikrein Gene Families", In: *Recent Progress on Kinins*, Birkhauser Verlag, Basel, pp. 19–25 (1992).

D. P. Bridon, et al., "Structural Comparison of Prostate–Specific Antigen and Human Glandular Kallikrein Using Molecular Modeling", *Urology*, 45, 801–806 (1995).

C. Chang, et al., "Solid Phase Peptide Synthesis Using Mild Base Cleavage of Nα–Fluorenylmethyloxycarbonylamino Acids, Exemplified by a Synthesis of Dihydrosomatostatin," *Int. J. Pept. Pro. Res.*, 11, 246–249 (1978).

P. Chapdelaine, "High Level of Expression in the Prostate of a Human Glandular kallikrein mRNA Related to Prostate–Specific Antigen", *FEBS Lett.*, 236, 205–208 (1988).

A. Christensson, et al., "Enzymatic Activity of Prostate–Specific Antigen and its Reactions with Extracellular Serine Proteinase Inhibitors", *Eur. J. Biochem.*, 194, 755–763 (1990).

A. Christensson, et al., "Serum Prostate Specific Antigen Complexed to α1–Antichymotrypsin as an Indicator of Prostate Cancer", *J. Urol.*, 150, 100–105 (1993).

J. Clements, "The Glandular Kallikrein Family of Enzymes: Tissue–Specific Expression and Hormonal Regulation", *Endocr. Rev.*, 10, 393–419 (1989).

J. A. Clements, et al., "The Human Kallikrein Gene Family: A Diversity of Expression and Function", *Mol. Cell Endocrinol.*, 99, c1–6 (1994).

P. Cohen, et al., "Biological Effects of PSA as an IGFBP–3 Protease", In: *Program and Abstracts, 74th Annual Meeting of the Endocrine Society*, San Antonio, TX, p. 291, Abstract No. 960 (Jun. 1992).

M. Digby, et al., "Human prostate specific antigen (PSA) gene: structure and linkage to the kallikrein–like gene", *Nuc. Acids Res.*, 17, 2137 (1989).

B. Evans, et al., "Structure and Chromosomal Localization of the Human Renal kallikrein Gene", *Biochemistry*, 27, 3124–3129 (1988).

(List continued on next page.)

Primary Examiner—Yvonne Eyler
Attorney, Agent, or Firm—Schwegman, Lundberg, Woessner & Kluth, P.A.

[57] ABSTRACT

An isolated, purified variant hK2 polypeptide useful in preparing immunogenic compositions and vaccines is provided. The variant hK2 polypeptides are more stable to purification than wild type mature hK2 polypeptide.

2 Claims, 21 Drawing Sheets

OTHER PUBLICATIONS

D. Fukushima, et al., "Nucleotide Sequence of Cloned DNA for Human Pancreatic Kallikrien", *Biochemistry*, 24, 8037–8043 (1985).

P. Henttu, et al., "cDNA Coding for the Entire Human prostate Specific Antigen Shows High Homologies to the Human Tissue Kallikriein Genes", *Biochemical and Biophysical Research Communications*, 160, 903–910 (Apr. 28, 1989).

P. Henttu, et al., "Expression of the Gene Coding for Human Prostate–Specific Antigen and Related hGK–1 in Benign and Malignant Tumors of the Human Prostate," *Int. J. Cancer*, 45, 654–660 (1990).

C. S. Hill, et al., "The Preparation of Monoclonal Antibodies Which React Preferentially with Human Bone Alkaline Phosphates and not Liver Alkaline Phosphatase," *Clinica Chemica Acta*, 186, 315–320 (1989).

T. H. Jones, et al., "Bioregulatory Role of the Kallikrein––Kinin System in the Normal Pituitary Gland and Its Tumours," *Acta Endocrinol.*, 127, 481–484 (1992).

C. Killian, et al., "Mitogenic Response of Osteoblast Cells to Prostate–Specific Antigen Suggests an Activation of Latent TGF–6 and a Proteolytic Modulation of Cell Adhesive Receptors," *Biochem. Biophys. Res. Comm.*, 192, 940 (1993).

J. Leinonen, et al., "Double–Label Time–Resolved Immunofluorometric Assay of Prostate–Specific Antigen and of its Complex with $\alpha 1$–Antichymotrypsin," *Clin. Chem.*, 39, 2098–2103 (1993).

J. Lovgren, et al., "Production of Recombinant PSA and HK2 and Analysis of Their Immunologic Cross–Reactivity," *Biochem. Biophys. Res. Comm.*, 231, 888–895 (1995).

H. Lu, et al., "Human urinary Kallikrein", *Int. J. Peptide Protein Res.*, 33, 237–249 (1989).

A. Lundwall, et al., "Molecular cloning of human prostate specific antigen cDNA", *FEBS Lett.*, 214, 317–322 (Apr., 1987).

A. Lundwall, "Characterization of the gene for Prostate–specific antigen, a human glandular kallikrein", *Biochem. Biophys. Research Comm.*, 161, 1151–1159 (Jun., 1989).

R. McCormack, et al., "Molecular Forms of Prostate–Specific Antigen and the Human Kallikrein Gene Family: A New Era", *Urology*, 45, 729–744 (May 1995).

B. Montgomery, et al., "Hormonal Regulation of Prostate–Specific Antigen (PSA) Glycoprotein in the Human Prostatic Adenocarcinoma Cell Line, LNCaP", *The Prostate*, 21, 63–73 (1992).

B. Morris, "hGK–1: A Kallikrein Gene Expressed in Human Prostate", *Clin. Exp. Pharmacol. Physiol*, 16, 345–351 (1989).

P. Murtha, et al., "hGK–1: A Kallikrein Gene Expressed in Human Prostate," *Biochemistry*, 32, 6459–6464 (1993).

G. Paradis, et al., "Looking for Human Glandular Kallikrein–1 in the Prostate", *The Prostate*, 15, 343–353 (1989).

S. Qui, et al., "In Situ Hybridization of Prostate–Specific Antigen mRNA in Human Prostate", *J. Urology*, 144, 1550–1556 (1990).

P. Riegman, et al., "Characterization of the Prostate–Specific Antigen Gene: A Novel Huamn Kallikrein–Like Gene", *Biochem. Biophys. Res. Comm.*, 159, 95–102 (Feb., 1989).

P. Riegman, et al., "The prostate–specific antigen gene and the human glandular kallikrein–1 gene are tandemly located on chromosome 19", *FEBS Lett.*, 247, 123–126 (Apr., 1989).

P. H. Riegman, et al., "Identification and androgen–regulated expression of two major human glandular kallikrein–1 (hGK–1) mRNA species", *Molecular and Cellular Endocrinology*, 76, 181–190 (1991).

M. S. Saedi, et al., "Overexpression of a human prostate–specific glandular kallikrein hK2, in *E. coli* and generation of antibodies", *Molecular and Cellular Endocrinology*, 109, 237–241 (Feb., 1995).

L. J. Schedlich, et al., "Kallikrein Genes: Cloning in Man and Expression in Rat Renal Hypertension", *Journal of Hypertension Supplement*, 6, S395–S398 (Dec., 1988).

L. Schedlich, et al., "Primary Structure of a Human Glandular Kallikrein Gene", *DNA*, 6, 429–437 (1987).

L. J. Schedlich, et al., "Three Alu Repeated Sequences Associated with a Human Glandular Kallikrein Gene", *Clin. Exper. Pharmacology & Physiology*, 15, 339–344 (1988).

P. Schulz, et al., "Sequence of a cDNA clone encompassing the complete mature human prostate specific antigen (PSA) and an unspliced leader sequence," *Nuc. Acids Res.*, 16, 6226 (1988).

G. Sutherland, et al., "Human prostate–specific antigen (APS) is a member of the glandular kallikrein gene family at 19p13", *Cytogenet. Cell Genet.*, 48, 205–207 (1988).

M. Vinhinen, "Modeling of Prostate Specific Antigen and Human Glandular Kallikrein Structures," *Biochem. Biophys. Res. Comm.*, 204, 1251–1256 (1994).

J. Wang, et al., "Purification and Characterization of recombinant tissue kallikrein from *Escherichia coli* and yeast", *Biochem. J.*, 276, 63–61 (1991).

K. Watt, et al., "Human prostate–specific antigen: structural and functional similarity with serine proteases", *Proc. Natl. Acad. Sci., USA*, 83, 3166–3170 (May, 1990).

C. Young, et al., "Androgenic Regulation of Kallikrein Gene Expression in Human Prostate Cells", *Abstracts, The Endocrine Society Annual Meeting* (1990).

C. Young, et al., "Tissue Specific and Hormonal Regulation of Human Prostate–Specific Glandular Kallikrein", *Biochemistry*, 31, 818–824 (1992).

C. F.–Y. Young, et al., "Hormonal Regulation of Prostate–Specific Antigen Messenger RNA in Human Prostatic Adenocarcinoma Cell Line LNCap", *Cancer Research*, 51, 3748–3752 (Jul., 1991).

C. Y.–F. Young, et al., "Expression and Androgenic Regulation of Human Prostate–Specific Kallikreins," *J. Androl*, 16, 97–99 (1995).

D. Deperthes, et al., "Isolation of Prostatic Kallikrein hK2, also Known as hGK–1, in Human Seminal Plasma", *Biochim. Biophys. Acta*, 1245, 311–316 (1995).

Ashley, P. L., et al., "Kallikrein–Related mRNAs of the Rat Submaxillary Gland: Nucleotide Sequences of Four Distinct Types Including Tonin", *Biochemistry*, 24, 4512–4520, (1985).

Ashley, P. L., et al., "Tissue–Specific Expression of Kallikrein–Related Genes in the Rat", *Biochemistry*, 24, 4520–4527, (1985).

Drinkwater, C. C., et al., "Kallikreins, Kinins and Growth Factor Biosynthesis", *TIBS*, 13, 169–172, (1988).

Husmann, D.A., et al., "Antipeptide Antibodies to Two Distinct Regions of the Androgen Receptor Localize the Receptor Protein to the Nuclei of Target Cells in the Rat and Human Prostate", *Endocrinology*, 126, 2359–2368 (1990).

Kuus–Reichel, K., et al., "Production of IgG Monoclonal Antibodies to the Tumor–Associated Antigen, CA–195", *Hybridoma*, 13, 31–36 (1994).

Lottspeich, F., et al., "N–Terminal Amino Acid Sequence of Human Urinary Kallikrein Homology with Other Serine Proteases", *Hoppe–Seyler's Z. Physiol. Chem.*, 360, 1947–1950, (Dec., 1979).

Luckow, V. A., et al., "Trends in the Development of Baculovirus Expression Vectors", *Bio/Technology*, 6, 47–55, (Jan., 1988).

Okaneya, T., et al., "Overexpression of a Prostate–Specific Glandular Kallikrein hK2 Protein Using a Baculovirus Expression System", Abstract, Soc. for Basic Urologic Res., Spring Meeting, (May 13–14, 1994).

Rahn, H. P., et al., "Expression of Human Salivary–Gland Kallikrein in Insect Cells by a Baculovirus Vector", *In: Recent Progress in Kinins,* Fritz, H., et al., (eds.), Birkhauser Verlag, Basel, 66–73, (1992).

Ransom, I.P., *Practical Competitive Binding Assay Methods,* C. V. Mosby Co., St. Louis, 1–9, 54–61, (1976).

Tijssen, P., "Practice and Theory of Enzyme Immunoassays", *In: Laboratory Techniques in Biochemistry and Molecular Biology,* 15, Burdon, R. H., (ed.), Elsevier, New York, 43–78, 95–121, 297–384, (1985).

van Leeuwen, B. H., et al., "Mouse Glandular Kallikrein Genes", *J. Bio. Chem.,* 261, 5529–5535, (1986).

Schedlich et al. DNA 6(5) 429–37, 1987.

Deguchi, T., et al., "Detection of Micrometastatic Prostate Cancer Cells in Lymph Nodes by Reverse Transcriptase- –Polymerase Chain Reaction", *Cancer Research,* 53, 5350–5354 (Nov. 15, 1993).

Fugger, L., et al., "Expression of HLA–DR4 and Human CD4 Transgenes in Mice Determines the Variable Region β–chain T–cell Repertoire and Mediates an HLA–DR–Restricted Immune Response", *Proc. Natl. Acad. Sci. USA,* 91, 6151–6155 (Jun. 1994).

Takayama, T.K., et al., "Newer Applications of Serum Prostate–Specific Antigen in the Management of Prostate Cancer", *Seminars in Oncology,* 21, 542–553 (Oct. 1994).

```
                                                      41
hK2: IVGGWECEKHSQPWQVAV SHGWAHCGGVLVHPQWVLTAAHCLKKNSQVWLGRHN
hK3: **************L*A*R*R*V***************IRNK*VIL****S

56
     LFEPEDTGQRVPVSHSFPHPLYNMSLLKHQSLRPDEDSSHDLMLLRLSEPAKIT
     _*H****VFQT****DNRF*GD**************EL*

110                                           153
     DVVKVLGLPTQEPALGTTCYASGWGSIEPEEFLRPRSLQCVSLHLLSNDMCA
     *A*MD*****************TPKKQVI*V

162  167
     RAYSEKVTEFMLCAGLWTGGKDTCGGDSGGPLVCNGVLQGITSWGPEPCALPEKP
     OVHPQ**K**R*SS******************S****R*

217           237
     AVYTKVVHYRKWIKDTIAANP
     SL**************V***
```

FIG. 1

FIG. 2 hK2 cDNA

```
           pphK2                                                                          phK2                       hK
        ┌──┐                                                                           ┌──┐                        ┌──┐
-76   CAGCATGTGGGACCTGGTTCTCTCCATCGCCTTGGTCTGTGGGGTGCACTGGTGCGTGCCCCTCATCCAGTCTCGGA
        1▶MetTrpAspLeuValLeuSerIleAlaLeuSerValGlyCysThrGlyAlaValProLeuIleGlnSerArg
                                                                                         1▶I
  2   TTGTGGGAGGCTGGAGTGTGAGAAGCATTCCAACCCTGGCTGTGTACAGTGTCATGGATGGGCACACTGT
      leValGlyGlyTrpGluCysGluLysHisSerGlnProTrpGlnValAlaValTyrSerHisGlyTrpAlaHisCys
 79   GGGGGTGTCCTGGTGCACCCCAGTGGTGCCATTGCCACGCTGCCCATAGAAGAATAGCCAGGTCTGGCTGGG
      GlyGlyValLeuValHisProGlnTrpValLeuThrAlaAlaHisCysLeuLysLysAsnSerGlnValTrpLeuGl
 27▶
156   TCGGCACAACCTGTTTGAGCCTGAAGACACAGGCCAGAGGGTCCCTGCAGCCACAGCTTCCCACACCCGCTCTACA
      yArgHisAsnLeuPheGluProGluAspThrGlyGlnArgValProValSerHisSerPheProHisProLeuTyrA
 52▶
233   ATATGAGCCTTCTGAAGCATCAAAGCCTTAGACCAGATGAAGACCTCAGCCATGAGCTCCTGCCCTGTCA
      snMetSerLeuLeuLysHisGlnSerLeuArgProAspGluAspLeuSerAspLeuMetLeuLeuArgLeuSer
 78▶
310   GAGCCTGCCAAGATACAGATGTTGTAGGTTGTGAAGGTTCTGCCCAGGAGCCTCAGCCATGAGCTCCTGCCCTGTCA
      GluProAlaLysIleThrAspAlaValLysValLeuProThrGlnGluProAlaLeuGlyThrThrCysTy
104▶
387   CGCCTCAGGCTGGGCAGCATCGAACCAGAGAGTTCTTGCGCCCAGGAGTCTTCAGTGTGTGAGCCTCCATCTCC
      rAlaSerGlyTrpGlySerIleGluProGluGluPheLeuArgProArgSerLeuGlnCysValSerLeuHisLeuL
129▶
464   TGTCCAATGACATGTGCTAGAGCTTACTCTGAGAAGGTGACAGAGTTCATGTTGTCTGGCCTCTGGACAGGT
      euSerAsnAspMetCysAlaArgAlaTyrSerGluLysValThrGluPheMetLeuCysAlaGlyLeuTrpThrGly
155▶
541   GGTAAAGACACATTGTGGGGGTGATTCTGAAAAGCCTGTGTGTACACCAAGGTGTGCATTACCGAAGTGATCAAGAC
      GlyLysAspThrCysLysGlyAspSerGlyGlyProLeuLeuCysAsnGlyValLeuGlnGlyIleThrSerTrpGly
181▶
618   CCCTGAGCCATGCTGCCCTGAAAAGCCTGCTGTGTACACCAAGGTGTGCATTACCGAAGTGATCAAGGAC
      yProGluProCysAlaLeuProGluLysProAlaValTyrThrLysValValHisTyrArgLysTrpIleLysAsp
206▶
694   ACCATGCAGCCAACCCCTGAGTGCCCT
232▶  ThrIleAlaAlaAsnPro•••ValPro
```

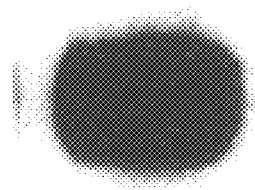
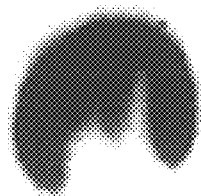
— 200kD
— 66kD
— 31kD
— 22kD
— 14kD
FIG. 8

1) CALPEKPAVY TKVVHY↓R̂↓KWI KDTIAAN

2) DRVY↓IHPFHLLVYS

3) VPLIQSR̂↓IVGGWEC

4) HCLKKNSQVWL↓GRHNL

5) FVNQHL̂↓CGSHLVEALYL̂↓VCGERGFFŶ↓TPKA

6) CSGKIVIAR̂↓YGKV↓F̂↓RGNK

▽ = PSA    ↓ = hK2

R= Arg; K= Lys; Y=Tyr; F= Phe; L= Leu; T= Thr

FIG. 16

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 237 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Ile Val Gly Gly Trp Glu Cys Glu Lys His Ser Gln Pro Trp Gln Val
1               5                   10                  15

Ala Val Tyr Ser His Gly Trp Ala His Cys Gly Gly Val Leu Val His
            20                  25                  30

Pro Gln Trp Val Leu Thr Ala Ala His Cys Leu Lys Lys Asn Ser Gln
        35                  40                  45

Val Trp Leu Gly Arg His Asn Leu Phe Glu Pro Glu Asp Thr Gly Gln
    50                  55                  60

Arg Val Pro Val Ser His Ser Phe Pro His Pro Leu Tyr Asn Met Ser
65                  70                  75                  80

Leu Leu Lys His Gln Ser Leu Arg Pro Asp Glu Asp Ser Ser His Asp
                85                  90                  95

Leu Met Leu Leu Arg Leu Ser Glu Pro Ala Lys Ile Thr Asp Val Val
            100                 105                 110

Lys Val Leu Gly Leu Pro Thr Gln Glu Pro Ala Leu Gly Thr Thr Cys
            115                 120                 125

Tyr Ala Ser Gly Trp Gly Ser Ile Glu Pro Glu Glu Phe Leu Arg Pro
        130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
            180                 185                 190

Leu Val Cys Asn Gly Val Leu Gln Gly Ile Thr Ser Trp Gly Pro Glu
        195                 200                 205

Pro Cys Ala Leu Pro Glu Lys Pro Val Val Tyr Thr Lys Val Val His
    210                 215                 220

Tyr Arg Lys Trp Ile Lys Asp Thr Ile Ala Ala Asn Pro
225                 230                 235
```

(2) INFORMATION FOR SEQ ID NO:2:

(i) SEQUENCE CHARACTERISTICS:
      (A) LENGTH: 711 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:2:

ATT GTG GGA GGC TGG GAG TGT GAG AAG CAT TCC CAA CCC TGG CAG GTG        48

```
Ile Val Gly Gly Trp Glu Cys Glu Lys His Ser Gln Pro Trp Gln Val
 1               5                  10                 15

GCT GTG TAC AGT CAT GGA TGG GCA CAC TGT GGG GGT GTC CTG GTG CAC        96
Ala Val Tyr Ser His Gly Trp Ala His Cys Gly Gly Val Leu Val His
             20                  25                  30

CCC CAG TGG GTG CTC ACA GCT GCC CAT TGC CTA AAG AAG AAT AGC CAG       144
Pro Gln Trp Val Leu Thr Ala Ala His Cys Leu Lys Lys Asn Ser Gln
         35                  40                  45

GTC TGG CTG GGT CGG CAC AAC CTG TTT GAG CCT GAA GAC ACA GGC CAG       192
Val Trp Leu Gly Arg His Asn Leu Phe Glu Pro Glu Asp Thr Gly Gln
     50                  55                  60

AGG GTC CCT GTC AGC CAC AGC TTC CCA CAC CCG CTC TAC AAT ATG AGC       240
Arg Val Pro Val Ser His Ser Phe Pro His Pro Leu Tyr Asn Met Ser
 65                  70                  75                  80

CTT CTG AAG CAT CAA AGC CTT AGA CCA GAT GAA GAC TCC AGC CAT GAC       288
Leu Leu Lys His Gln Ser Leu Arg Pro Asp Glu Asp Ser Ser His Asp
                 85                  90                  95

CTC ATG CTG CTC CGC CTG TCA GAG CCT GCC AAG ATC ACA GAT GTT GTG       336
Leu Met Leu Leu Arg Leu Ser Glu Pro Ala Lys Ile Thr Asp Val Val
             100                 105                 110

AAG GTC CTG GGC CTG CCC ACC CAG GAG CCA GCA CTG GGG ACC ACC TGC       384
Lys Val Leu Gly Leu Pro Thr Gln Glu Pro Ala Leu Gly Thr Thr Cys
         115                 120                 125

TAC GCC TCA GGC TGG GGC AGC ATC GAA CCA GAG GAG TTC TTG CGC CCC       432
Tyr Ala Ser Gly Trp Gly Ser Ile Glu Pro Glu Glu Phe Leu Arg Pro
    130                 135                 140

AGG AGT CTT CAG TGT GTG AGC CTC CAT CTC CTG TCC AAT GAC ATG TGT       480
Arg Ser Leu Gln Cys Val Ser Leu His Leu Leu Ser Asn Asp Met Cys
145                 150                 155                 160

GCT AGA GCT TAC TCT GAG AAG GTG ACA GAG TTC ATG TTG TGT GCT GGG       528
Ala Arg Ala Tyr Ser Glu Lys Val Thr Glu Phe Met Leu Cys Ala Gly
                165                 170                 175

CTC TGG ACA GGT GGT AAA GAC ACT TGT GGG GGT GAT TCT GGG GGT CCA       576
Leu Trp Thr Gly Gly Lys Asp Thr Cys Gly Gly Asp Ser Gly Gly Pro
            180                 185                 190

CTT GTC TGT AAT GGT GTG CTT CAA GGT ATC ACA TCA TGG GGC CCT GAG       624
Leu Val Cys Asn Gly Val Leu Gln Gly Ile Thr Ser Trp Gly Pro Glu
        195                 200                 205

CCA TGT GCC CTG CCT GAA AAG CCT GTT GTG TAC ACC AAG GTG GTG CAT       672
Pro Cys Ala Leu Pro Glu Lys Pro Val Val Tyr Thr Lys Val Val His
    210                 215                 220

TAC CGG AAG TGG ATC AAG GAC ACC ATC GCA GCC AAC CCC                   711
Tyr Arg Lys Trp Ile Lys Asp Thr Ile Ala Ala Asn Pro
225                 230                 235

(2) INFORMATION FOR SEQ ID NO:3:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:3:

Met Trp Asp Leu Val Leu Ser Ile Ala Leu Ser Val Gly Cys Thr Gly
 1               5                  10                  15

Ala Val Pro Leu Ile Gln Ser Arg Ile Val Gly Gly Trp Glu Cys Glu
             20                  25                  30

Lys His Ser Gln Pro Trp Gln Val Ala Val Tyr Ser His Gly Trp Ala
         35                  40                  45
```

```
His Cys Gly Gly Val Leu Val His Pro Gln Trp Val Leu Thr Ala Ala
 50                  55                  60

His Cys Leu Lys Lys Asn Ser Gln Val Trp Leu Gly Arg His Asn Leu
 65                  70                  75                  80

Phe Glu Pro Glu Asp Thr Gly Gln Arg Val Pro Val Ser His Ser Phe
                 85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
            115                 120                 125

Pro Ala Lys Ile Thr Asp Val Val Lys Val Leu Gly Leu Pro Thr Gln
            130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
            195                 200                 205

Cys Gly Gly Asp Ser Gly Gly Pro Leu Val Cys Asn Gly Val Leu Gln
210                 215                 220

Gly Ile Thr Ser Trp Gly Pro Glu Pro Cys Ala Leu Pro Glu Lys Pro
225                 230                 235                 240

Val Val Tyr Thr Lys Val Val His Tyr Arg Lys Trp Ile Lys Asp Thr
                245                 250                 255

Ile Ala Ala Asn Pro
            260

(2) INFORMATION FOR SEQ ID NO:4:

(i) SEQUENCE CHARACTERISTICS:
        (A) LENGTH: 832 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 10..792

(xi) SEQUENCE DESCRIPTION: SEQ ID NO:4:

GGATCCAGC ATG TGG GAC CTG GTT CTC TCC ATC GCC TTG TCT GTG GGG         48
          Met Trp Asp Leu Val Leu Ser Ile Ala Leu Ser Val Gly
            1               5                  10

TGC ACT GGT GCC GTG CCC CTC ATC CAG TCT CGG ATT GTG GGA GGC TGG      96
Cys Thr Gly Ala Val Pro Leu Ile Gln Ser Arg Ile Val Gly Gly Trp
 15                  20                  25

GAG TGT GAG AAG CAT TCC CAA CCC TGG CAG GTG GCT GTG TAC AGT CAT     144
Glu Cys Glu Lys His Ser Gln Pro Trp Gln Val Ala Val Tyr Ser His
 30                  35                  40                  45

GGA TGG GCA CAC TGT GGG GGT GTC CTG GTG CAC CCC CAG TGG GTG CTC     192
Gly Trp Ala His Cys Gly Gly Val Leu Val His Pro Gln Trp Val Leu
             50                  55                  60

ACA GCT GCC CAT TGC CTA AAG AAG AAT AGC CAG GTC TGG CTG GGT CGG     240
Thr Ala Ala His Cys Leu Lys Lys Asn Ser Gln Val Trp Leu Gly Arg
             65                  70                  75
```

```
CAC AAC CTG TTT GAG CCT GAA GAC ACA GGC CAG AGG GTC CCT GTC AGC        288
His Asn Leu Phe Glu Pro Glu Asp Thr Gly Gln Arg Val Pro Val Ser
            80                  85                  90

CAC AGC TTC CCA CAC CCG CTC TAC AAT ATG AGC CTT CTG AAG CAT CAA        336
His Ser Phe Pro His Pro Leu Tyr Asn Met Ser Leu Leu Lys His Gln
        95                 100                 105

AGC CTT AGA CCA GAT GAA GAC TCC AGC CAT GAC CTC ATG CTG CTC CGC        384
Ser Leu Arg Pro Asp Glu Asp Ser Ser His Asp Leu Met Leu Leu Arg
110                 115                 120                 125

CTG TCA GAG CCT GCC AAG ATC ACA GAT GTT GTG AAG GTC CTG GGC CTG        432
Leu Ser Glu Pro Ala Lys Ile Thr Asp Val Val Lys Val Leu Gly Leu
                130                 135                 140

CCC ACC CAG GAG CCA GCA CTG GGG ACC ACC TGC TAC GCC TCA GGC TGG        480
Pro Thr Gln Glu Pro Ala Leu Gly Thr Thr Cys Tyr Ala Ser Gly Trp
            145                 150                 155

GGC AGC ATC GAA CCA GAG GAG TTC TTG CGC CCC AGG AGT CTT CAG TGT        528
Gly Ser Ile Glu Pro Glu Glu Phe Leu Arg Pro Arg Ser Leu Gln Cys
        160                 165                 170

GTG AGC CTC CAT CTC CTG TCC AAT GAC ATG TGT GCT AGA GCT TAC TCT        576
Val Ser Leu His Leu Leu Ser Asn Asp Met Cys Ala Arg Ala Tyr Ser
175                 180                 185

GAG AAG GTG ACA GAG TTC ATG TTG TGT GCT GGG CTC TGG ACA GGT GGT        624
Glu Lys Val Thr Glu Phe Met Leu Cys Ala Gly Leu Trp Thr Gly Gly
190                 195                 200                 205

AAA GAC ACT TGT GGG GGT GAT TCT GGG GGT CCA CTT GTC TGT AAT GGT        672
Lys Asp Thr Cys Gly Gly Asp Ser Gly Gly Pro Leu Val Cys Asn Gly
                210                 215                 220

GTG CTT CAA GGT ATC ACA TCA TGG GGC CCT GAG CCA TGT GCC CTG CCT        720
Val Leu Gln Gly Ile Thr Ser Trp Gly Pro Glu Pro Cys Ala Leu Pro
            225                 230                 235

GAA AAG CCT GTT GTG TAC ACC AAG GTG GTG CAT TAC CGG AAG TGG ATC        768
Glu Lys Pro Val Val Tyr Thr Lys Val Val His Tyr Arg Lys Trp Ile
        240                 245                 250

AAG GAC ACC ATC GCA GCC AAC CCC TGAGTGCCCC TGTCCCACCC CTACCTCTAG       822
Lys Asp Thr Ile Ala Ala Asn Pro
    255                 260

TAAACTGCAG                                                             832

(2) INFORMATION FOR SEQ ID NO:5:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO:5:

Val Pro Leu Ile Gln Ser Arg Ile Val Gly Gly Trp Glu Cys Glu Lys
 1               5                  10                  15

His Ser Gln Pro Trp Gln Val Ala Val Tyr Ser His Gly Trp Ala His
                20                  25                  30

Cys Gly Gly Val Leu Val His Pro Gln Trp Val Leu Thr Ala Ala His
            35                  40                  45

Cys Leu Lys Lys Asn Ser Gln Val Trp Leu Gly Arg His Asn Leu Phe
        50                  55                  60

Glu Pro Glu Asp Thr Gly Gln Arg Val Pro Val Ser His Ser Phe Pro
65                  70                  75                  80

His Pro Leu Tyr Asn Met Ser Leu Leu Lys His Gln Ser Leu Arg Pro
```

```
                       85                  90                    95
Asp Glu Asp Ser Ser His Asp Leu Met Leu Leu Arg Leu Ser Glu Pro
            100                 105                 110

Ala Lys Ile Thr Asp Val Val Lys Val Leu Gly Leu Pro Thr Gln Glu
            115                 120                 125

Pro Ala Leu Gly Thr Thr Cys Tyr Ala Ser Gly Trp Gly Ser Ile Glu
            130                 135                 140

Pro Glu Glu Phe Leu Arg Pro Arg Ser Leu Gln Cys Val Ser Leu His
145                 150                 155                 160

Leu Leu Ser Asn Asp Met Cys Ala Arg Ala Tyr Ser Glu Lys Val Thr
                165                 170                 175

Glu Phe Met Leu Cys Ala Gly Leu Trp Thr Gly Lys Asp Thr Cys
            180                 185                 190

Gly Gly Asp Ser Gly Gly Pro Leu Val Cys Asn Gly Val Leu Gln Gly
                195                 200                 205

Ile Thr Ser Trp Gly Pro Glu Pro Cys Ala Leu Pro Glu Lys Pro Val
            210                 215                 220

Val Tyr Thr Lys Val Val His Tyr Arg Lys Trp Ile Lys Asp Thr Ile
225                 230                 235                 240

Ala Ala Asn Pro (2) INFORMATION FOR SEQ ID NO:6:

(i) SEQUENCE CHARACTERISTICS:
        (A) LENGTH: 766 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..732

(xi) SEQUENCE DESCRIPTION: SEQ ID NO:6:

GTG CCC CTC ATC CAG TCT CGG ATT GTG GGA GGC TGG GAG TGT GAG AAG      48
Val Pro Leu Ile Gln Ser Arg Ile Val Gly Gly Trp Glu Cys Glu Lys
  1               5                  10                  15

CAT TCC CAA CCC TGG CAG GTG GCT GTG TAC AGT CAT GGA TGG GCA CAC      96
His Ser Gln Pro Trp Gln Val Ala Val Tyr Ser His Gly Trp Ala His
             20                  25                  30

TGT GGG GGT GTC CTG GTG CAC CCC CAG TGG GTG CTC ACA GCT GCC CAT     144
Cys Gly Gly Val Leu Val His Pro Gln Trp Val Leu Thr Ala Ala His
         35                  40                  45

TGC CTA AAG AAG AAT AGC CAG GTC TGG CTG GGT CGG CAC AAC CTG TTT     192
Cys Leu Lys Lys Asn Ser Gln Val Trp Leu Gly Arg His Asn Leu Phe
     50                  55                  60

GAG CCT GAA GAC ACA GGC CAG AGG GTC CCT GTC AGC CAC AGC TTC CCA     240
Glu Pro Glu Asp Thr Gly Gln Arg Val Pro Val Ser His Ser Phe Pro
 65                  70                  75                  80

CAC CCG CTC TAC AAT ATG AGC CTT CTG AAG CAT CAA AGC CTT AGA CCA     288
His Pro Leu Tyr Asn Met Ser Leu Leu Lys His Gln Ser Leu Arg Pro
                 85                  90                  95

GAT GAA GAC TCC AGC CAT GAC CTC ATG CTG CTC CGC CTG TCA GAG CCT     336
Asp Glu Asp Ser Ser His Asp Leu Met Leu Leu Arg Leu Ser Glu Pro
            100                 105                 110

GCC AAG ATC ACA GAT GTT GTG AAG GTC CTG GGC CTG CCC ACC CAG GAG     384
Ala Lys Ile Thr Asp Val Val Lys Val Leu Gly Leu Pro Thr Gln Glu
            115                 120                 125
```

```
CCA GCA CTG GGG ACC ACC TGC TAC GCC TCA GGC TGG GGC AGC ATC GAA      432
Pro Ala Leu Gly Thr Thr Cys Tyr Ala Ser Gly Trp Gly Ser Ile Glu
    130                 135                 140

CCA GAG GAG TTC TTG CGC CCC AGG AGT CTT CAG TGT GTG AGC CTC CAT      480
Pro Glu Glu Phe Leu Arg Pro Arg Ser Leu Gln Cys Val Ser Leu His
145                 150                 155                 160

CTC CTG TCC AAT GAC ATG TGT GCT AGA GCT TAC TCT GAG AAG GTG ACA      528
Leu Leu Ser Asn Asp Met Cys Ala Arg Ala Tyr Ser Glu Lys Val Thr
                165                 170                 175

GAG TTC ATG TTG TGT GCT GGG CTC TGG ACA GGT GGT AAA GAC ACT TGT      576
Glu Phe Met Leu Cys Ala Gly Leu Trp Thr Gly Gly Lys Asp Thr Cys
            180                 185                 190

GGG GGT GAT TCT GGG GGT CCA CTT GTC TGT AAT GGT GTG CTT CAA GGT      624
Gly Gly Asp Ser Gly Gly Pro Leu Val Cys Asn Gly Val Leu Gln Gly
        195                 200                 205

ATC ACA TCA TGG GGC CCT GAG CCA TGT GCC CTG CCT GAA AAG CCT GTT      672
Ile Thr Ser Trp Gly Pro Glu Pro Cys Ala Leu Pro Glu Lys Pro Val
210                 215                 220

GTG TAC ACC AAG GTG GTG CAT TAC CGG AAG TGG ATC AAG GAC ACC ATC      720
Val Tyr Thr Lys Val Val His Tyr Arg Lys Trp Ile Lys Asp Thr Ile
225                 230                 235                 240

GCA GCC AAC CCC TGAGTGCCCC TGTCCCACCC CTACCTCTAG TAAA                766
Ala Ala Asn Pro (2) INFORMATION FOR SEQ ID NO:7:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
```

|           |     | 180 |     |     |     | 185 |     |     |     | 190 |     |
|-----------|-----|-----|-----|-----|-----|-----|-----|-----|-----|-----|-----|
| Leu Val Cys Asn Gly Val Leu Gln Gly Ile Thr Ser Trp Gly Ser Glu |

Leu Val Cys Asn Gly Val Leu Gln Gly Ile Thr Ser Trp Gly Ser Glu
            195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACGCGGATCC AGCATGTGGG ACCTGGTTCT CT                                32

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ACAGCTGCAG TTTACTAGAG GTAGGGGTGG GAC                               33

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

ATATGGATCC ATATGTCAGC ATGTGGGACC TGGTTCTCTC CA                     42

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ATATGGATCC TCAGGGGTTG GCTGCGATGG T                                 31

(2) INFORMATION FOR SEQ ID NO:12:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

| Ile | Val | Gly | Gly | Trp | Glu | Cys | Glu | Lys | His | Ser | Gln | Pro | Trp | Gln | Val |
|---|---|---|---|---|---|---|---|---|---|---|---|---|---|---|---|
| 1 | | | | 5 | | | | | 10 | | | | | 15 | |

| Ala | Val | Tyr | Ser | His | Gly | Trp | Ala | His | Cys | Gly | Gly | Val | Leu | Val | His |
|---|---|---|---|---|---|---|---|---|---|---|---|---|---|---|---|
| | | | 20 | | | | | 25 | | | | | 30 | | |

| Pro | Gln | Trp | Val | Leu | Thr | Ala | Ala | His | Cys | Leu | Lys | Lys | Asn | Ser | Gln |
|---|---|---|---|---|---|---|---|---|---|---|---|---|---|---|---|
| | | | 35 | | | | | 40 | | | | | 45 | | |

| Val | Trp | Leu | Gly | Arg | His | Asn | Leu | Phe | Glu | Pro | Glu | Asp | Thr | Gly | Gln |
|---|---|---|---|---|---|---|---|---|---|---|---|---|---|---|---|
| | 50 | | | | | 55 | | | | | 60 | | | | |

| Arg | Val | Pro | Val | Ser | His | Ser | Phe | Pro | His | Pro | Leu | Tyr | Asn | Met | Ser |
|---|---|---|---|---|---|---|---|---|---|---|---|---|---|---|---|
| 65 | | | | | 70 | | | | | 75 | | | | | 80 |

| Leu | Leu | Lys | His | Gln | Ser | Leu | Arg | Pro | Asp | Glu | Asp | Ser | Ser | His | Asp |
|---|---|---|---|---|---|---|---|---|---|---|---|---|---|---|---|
| | | | | 85 | | | | | 90 | | | | | 95 | |

| Leu | Met | Leu | Leu | Arg | Leu | Ser | Glu | Pro | Ala | Lys | Ile | Thr | Asp | Val | Val |
|---|---|---|---|---|---|---|---|---|---|---|---|---|---|---|---|
| | | | 100 | | | | | 105 | | | | | 110 | | |

| Lys | Val | Leu | Gly | Leu | Pro | Thr | Gln | Glu | Pro | Ala | Leu | Gly | Thr | Thr | Cys |
|---|---|---|---|---|---|---|---|---|---|---|---|---|---|---|---|
| | | | 115 | | | | | 120 | | | | | 125 | | |

| Tyr | Ala | Ser | Gly | Trp | Gly | Ser | Ile | Glu | Pro | Glu | Glu | Phe | Leu | Arg | Pro |
|---|---|---|---|---|---|---|---|---|---|---|---|---|---|---|---|
| | 130 | | | | | 135 | | | | | 140 | | | | |

| Arg | Ser | Leu | Gln | Cys | Val | Ser | Leu | His | Leu | Leu | Ser | Asn | Asp | Met | Cys |
|---|---|---|---|---|---|---|---|---|---|---|---|---|---|---|---|
| 145 | | | | | 150 | | | | | 155 | | | | | 160 |

| Ala | Arg | Ala | Tyr | Ser | Glu | Lys | Val | Thr | Glu | Phe | Met | Leu | Cys | Ala | Gly |
|---|---|---|---|---|---|---|---|---|---|---|---|---|---|---|---|
| | | | | 165 | | | | | 170 | | | | | 175 | |

| Leu | Trp | Thr | Gly | Gly | Lys | Asp | Thr | Cys | Gly | Gly | Asp | Ser | Gly | Gly | Pro |
|---|---|---|---|---|---|---|---|---|---|---|---|---|---|---|---|
| | | | 180 | | | | | 185 | | | | | 190 | | |

| Leu | Val | Cys | Asn | Gly | Val | Leu | Gln | Gly | Ile | Thr | Ser | Trp | Gly | Pro | Glu |
|---|---|---|---|---|---|---|---|---|---|---|---|---|---|---|---|
| | | | 195 | | | | | 200 | | | | | 205 | | |

| Pro | Cys | Ala | Leu | Pro | Glu | Lys | Pro | Ala | Val | Tyr | Thr | Lys | Val | Val | His |
|---|---|---|---|---|---|---|---|---|---|---|---|---|---|---|---|
| | 210 | | | | | 215 | | | | | 220 | | | | |

| Tyr | Arg | Lys | Trp | Ile | Lys | Asp | Thr | Ile | Ala | Ala | Asn | Pro |
|---|---|---|---|---|---|---|---|---|---|---|---|---|
| 225 | | | | | 230 | | | | | 235 | | |

(2) INFORMATION FOR SEQ ID NO:13:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION:SEQ ID NO:13:

```
ATT GTG GGA GGC TGG GAG TGT GAG AAG CAT TCC CAA CCC TGG CAG GTG        48
Ile Val Gly Gly Trp Glu Cys Glu Lys His Ser Gln Pro Trp Gln Val
 1               5                  10                  15

GCT GTG TAC AGT CAT GGA TGG GCA CAC TGT GGG GGT GTC CTG GTG CAC        96
Ala Val Tyr Ser His Gly Trp Ala His Cys Gly Gly Val Leu Val His
                20                  25                  30

CCC CAG TGG GTG CTC ACA GCT GCC CAT TGC CTA AAG AAG AAT AGC CAG       144
Pro Gln Trp Val Leu Thr Ala Ala His Cys Leu Lys Lys Asn Ser Gln
                35                  40                  45

GTC TGG CTG GGT CGG CAC AAC CTG TTT GAG CCT GAA GAC ACA GGC CAG       192
Val Trp Leu Gly Arg His Asn Leu Phe Glu Pro Glu Asp Thr Gly Gln
    50                  55                  60
```

```
AGG GTC CCT GTC AGC CAC AGC TTC CCA CAC CCG CTC TAC AAT ATG AGC      240
Arg Val Pro Val Ser His Ser Phe Pro His Pro Leu Tyr Asn Met Ser
 65              70                  75                  80

CTT CTG AAG CAT CAA AGC CTT AGA CCA GAT GAA GAC TCC AGC CAT GAC      288
Leu Leu Lys His Gln Ser Leu Arg Pro Asp Glu Asp Ser Ser His Asp
                 85                  90                  95

CTC ATG CTG CTC CGC CTG TCA GAG CCT GCC AAG ATC ACA GAT GTT GTG      336
Leu Met Leu Leu Arg Leu Ser Glu Pro Ala Lys Ile Thr Asp Val Val
            100                 105                 110

AAG GTC CTG GGC CTG CCC ACC CAG GAG CCA GCA CTG GGG ACC ACC TGC      384
Lys Val Leu Gly Leu Pro Thr Gln Glu Pro Ala Leu Gly Thr Thr Cys
        115                 120                 125

TAC GCC TCA GGC TGG GGC AGC ATC GAA CCA GAG GAG TTC TTG CGC CCC      432
Tyr Ala Ser Gly Trp Gly Ser Ile Glu Pro Glu Glu Phe Leu Arg Pro
    130                 135                 140

AGG AGT CTT CAG TGT GTG AGC CTC CAT CTC CTG TCC AAT GAC ATG TGT      480
Arg Ser Leu Gln Cys Val Ser Leu His Leu Leu Ser Asn Asp Met Cys
145                 150                 155                 160

GCT AGA GCT TAC TCT GAG AAG GTG ACA GAG TTC ATG TTG TGT GCT GGG      528
Ala Arg Ala Tyr Ser Glu Lys Val Thr Glu Phe Met Leu Cys Ala Gly
                165                 170                 175

CTC TGG ACA GGT GGT AAA GAC ACT TGT GGG GGT GAT TCT GGG GGT CCA      576
Leu Trp Thr Gly Gly Lys Asp Thr Cys Gly Gly Asp Ser Gly Gly Pro
            180                 185                 190

CTT GTC TGT AAT GGT GTG CTT CAA GGT ATC ACA TCA TGG GGC CCT GAG      624
Leu Val Cys Asn Gly Val Leu Gln Gly Ile Thr Ser Trp Gly Pro Glu
        195                 200                 205

CCA TGT GCC CTG CCT GAA AAG CCT GCT GTG TAC ACC AAG GTG GTG CAT      672
Pro Cys Ala Leu Pro Glu Lys Pro Ala Val Tyr Thr Lys Val Val His
    210                 215                 220

TAC CGG AAG TGG ATC AAG GAC ACC ATC GCA GCC AAC CCC                  711
Tyr Arg Lys Trp Ile Lys Asp Thr Ile Ala Ala Asn Pro
225                 230                 235

(2) INFORMATION FOR SEQ ID NO:14:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:14:

Met Trp Asp Leu Val Leu Ser Ile Ala Leu Ser Val Gly Cys Thr Gly
 1               5                  10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
 65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125
```

```
Pro Ala Lys Ile Thr Asp Val Val Lys Val Leu Gly Leu Pro Thr Gln
    130                 135                 140
Glu Pro Ala Leu Gly Thr Thr Cys Tyr Ala Ser Gly Trp Gly Ser Ile
145                 150                 155                 160
Glu Pro Glu Glu Phe Leu Arg Pro Arg Ser Leu Gln Cys Val Ser Leu
                165                 170                 175
His Leu Leu Ser Asn Asp Met Cys Ala Arg Ala Tyr Ser Glu Lys Val
            180                 185                 190
Thr Glu Phe Met Leu Cys Ala Gly Leu Trp Thr Gly Gly Lys Asp Thr
        195                 200                 205
Cys Gly Gly Asp Ser Gly Gly Pro Leu Val Cys Asn Gly Val Leu Gln
    210                 215                 220
Gly Ile Thr Ser Trp Gly Pro Glu Pro Cys Ala Leu Pro Glu Lys Pro
225                 230                 235                 240
Ala Val Tyr Thr Lys Val Val His Tyr Arg Lys Trp Ile Lys Asp Thr
                245                 250                 255
Ile Ala Ala Asn Pro
            260

(2) INFORMATION FOR SEQ ID NO:15:

(i) SEQUENCE CHARACTERISTICS:
        (A) LENGTH: 832 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 10..792

(xi) SEQUENCE DESCRIPTION: SEQ ID NO:15:

GGATCCAGC ATG TGG GAC CTG GTT CTC TCC ATC GCC TTG TCT GTG GGG           48
          Met Trp Asp Leu Val Leu Ser Ile Ala Leu Ser Val Gly
            1               5                  10

TGC ACT GGT GCC GTG CCC CTC ATC CAG TCT CGG ATT GTG GGA GGC TGG         96
Cys Thr Gly Ala Val Pro Leu Ile Gln Ser Arg Ile Val Gly Gly Trp
 15                  20                  25

GAG TGT GAG AAG CAT TCC CAA CCC TGG CAG GTG GCT GTG TAC AGT CAT        144
Glu Cys Glu Lys His Ser Gln Pro Trp Gln Val Ala Val Tyr Ser His
 30                  35                  40                  45

GGA TGG GCA CAC TGT GGG GGT GTC CTG GTG CAC CCC CAG TGG GTG CTC        192
Gly Trp Ala His Cys Gly Gly Val Leu Val His Pro Gln Trp Val Leu
                 50                  55                  60

ACA GCT GCC CAT TGC CTA AAG AAG AAT AGC CAG GTC TGG CTG GGT CGG        240
Thr Ala Ala His Cys Leu Lys Lys Asn Ser Gln Val Trp Leu Gly Arg
             65                  70                  75

CAC AAC CTG TTT GAG CCT GAA GAC ACA GGC CAG AGG GTC CCT GTC AGC        288
His Asn Leu Phe Glu Pro Glu Asp Thr Gly Gln Arg Val Pro Val Ser
         80                  85                  90

CAC AGC TTC CCA CAC CCG CTC TAC AAT ATG AGC CTT CTG AAG CAT CAA        336
His Ser Phe Pro His Pro Leu Tyr Asn Met Ser Leu Leu Lys His Gln
     95                 100                 105

AGC CTT AGA CCA GAT GAA GAC TCC AGC CAT GAC CTC ATG CTG CTC CGC        384
Ser Leu Arg Pro Asp Glu Asp Ser Ser His Asp Leu Met Leu Leu Arg
110                 115                 120                 125

CTG TCA GAG CCT GCC AAG ATC ACA GAT GTT GTG AAG GTC CTG GGC CTG        432
Leu Ser Glu Pro Ala Lys Ile Thr Asp Val Val Lys Val Leu Gly Leu
```

```
CCC ACC CAG GAG CCA GCA CTG GGG ACC ACC TGC TAC GCC TCA GGC TGG        480
Pro Thr Gln Glu Pro Ala Leu Gly Thr Thr Cys Tyr Ala Ser Gly Trp
            145                 150                 155

GGC AGC ATC GAA CCA GAG GAG TTC TTG CGC CCC AGG AGT CTT CAG TGT        528
Gly Ser Ile Glu Pro Glu Glu Phe Leu Arg Pro Arg Ser Leu Gln Cys
            160                 165                 170

GTG AGC CTC CAT CTC CTG TCC AAT GAC ATG TGT GCT AGA GCT TAC TCT        576
Val Ser Leu His Leu Leu Ser Asn Asp Met Cys Ala Arg Ala Tyr Ser
175                 180                 185

GAG AAG GTG ACA GAG TTC ATG TTG TGT GCT GGG CTC TGG ACA GGT GGT        624
Glu Lys Val Thr Glu Phe Met Leu Cys Ala Gly Leu Trp Thr Gly Gly
190                 195                 200                 205

AAA GAC ACT TGT GGG GGT GAT TCT GGG GGT CCA CTT GTC TGT AAT GGT        672
Lys Asp Thr Cys Gly Gly Asp Ser Gly Gly Pro Leu Val Cys Asn Gly
            210                 215                 220

GTG CTT CAA GGT ATC ACA TCA TGG GGC CCT GAG CCA TGT GCC CTG CCT        720
Val Leu Gln Gly Ile Thr Ser Trp Gly Pro Glu Pro Cys Ala Leu Pro
            225                 230                 235

GAA AAG CCT GCT GTG TAC ACC AAG GTG GTG CAT TAC CGG AAG TGG ATC        768
Glu Lys Pro Ala Val Tyr Thr Lys Val Val His Tyr Arg Lys Trp Ile
            240                 245                 250

AAG GAC ACC ATC GCA GCC AAC CCC TGAGTGCCCC TGTCCCACCC CTACCTCTAG       822
Lys Asp Thr Ile Ala Ala Asn Pro
255                 260

TAAACTGCAG                                                             832

(2) INFORMATION FOR SEQ ID NO:16:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO:16:

Val Pro Leu Ile Gln Ser Arg Ile Val Gly Gly Trp Glu Cys Glu Lys
1               5                   10                  15

His Ser Gln Pro Trp Gln Val Ala Val Tyr Ser His Gly Trp Ala His
            20                  25                  30

Cys Gly Gly Val Leu Val His Pro Gln Trp Val Leu Thr Ala Ala His
        35                  40                  45

Cys Leu Lys Lys Asn Ser Gln Val Trp Leu Gly Arg His Asn Leu Phe
    50                  55                  60

Glu Pro Glu Asp Thr Gly Gln Arg Val Pro Val Ser His Ser Phe Pro
65                  70                  75                  80

His Pro Leu Tyr Asn Met Ser Leu Leu Lys His Gln Ser Leu Arg Pro
                85                  90                  95

Asp Glu Asp Ser Ser His Asp Leu Met Leu Leu Arg Leu Ser Glu Pro
            100                 105                 110

Ala Lys Ile Thr Asp Val Val Lys Val Leu Gly Leu Pro Thr Gln Glu
        115                 120                 125

Pro Ala Leu Gly Thr Thr Cys Tyr Ala Ser Gly Trp Gly Ser Ile Glu
    130                 135                 140

Pro Glu Glu Phe Leu Arg Pro Arg Ser Leu Gln Cys Val Ser Leu His
145                 150                 155                 160

Leu Leu Ser Asn Asp Met Cys Ala Arg Ala Tyr Ser Glu Lys Val Thr
```

```
                     165                 170                 175
Glu Phe Met Leu Cys Ala Gly Leu Trp Thr Gly Gly Lys Asp Thr Cys
                 180                 185                 190

Gly Gly Asp Ser Gly Pro Leu Val Cys Asn Gly Val Leu Gln Gly
             195                 200                 205

Ile Thr Ser Trp Gly Pro Glu Pro Cys Ala Leu Pro Glu Lys Pro Ala
         210                 215                 220

Val Tyr Thr Lys Val Val His Tyr Arg Lys Trp Ile Lys Asp Thr Ile
225                 230                 235                 240

Ala Ala Asn Pro (2) INFORMATION FOR SEQ ID NO:17:

(i) SEQUENCE CHARACTERISTICS:
        (A) LENGTH: 766 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..732

(xi) SEQUENCE DESCRIPTION: SEQ ID NO:17:

GTG CCC CTC ATC CAG TCT CGG ATT GTG GGA GGC TGG GAG TGT GAG AAG      48
Val Pro Leu Ile Gln Ser Arg Ile Val Gly Gly Trp Glu Cys Glu Lys
  1               5                  10                  15

CAT TCC CAA CCC TGG CAG GTG GCT GTG TAC AGT CAT GGA TGG GCA CAC      96
His Ser Gln Pro Trp Gln Val Ala Val Tyr Ser His Gly Trp Ala His
                 20                  25                  30

TGT GGG GGT GTC CTG GTG CAC CCC CAG TGG GTG CTC ACA GCT GCC CAT     144
Cys Gly Gly Val Leu Val His Pro Gln Trp Val Leu Thr Ala Ala His
             35                  40                  45

TGC CTA AAG AAG AAT AGC CAG GTC TGG CTG GGT CGG CAC AAC CTG TTT     192
Cys Leu Lys Lys Asn Ser Gln Val Trp Leu Gly Arg His Asn Leu Phe
         50                  55                  60

GAG CCT GAA GAC ACA GGC CAG AGG GTC CCT GTC AGC CAC AGC TTC CCA     240
Glu Pro Glu Asp Thr Gly Gln Arg Val Pro Val Ser His Ser Phe Pro
 65                  70                  75                  80

CAC CCG CTC TAC AAT ATG AGC CTT CTG AAG CAT CAA AGC CTT AGA CCA     288
His Pro Leu Tyr Asn Met Ser Leu Leu Lys His Gln Ser Leu Arg Pro
                 85                  90                  95

GAT GAA GAC TCC AGC CAT GAC CTC ATG CTG CTC CGC CTG TCA GAG CCT     336
Asp Glu Asp Ser Ser His Asp Leu Met Leu Leu Arg Leu Ser Glu Pro
            100                 105                 110

GCC AAG ATC ACA GAT GTT GTG AAG GTC CTG GGC CTG CCC ACC CAG GAG     384
Ala Lys Ile Thr Asp Val Val Lys Val Leu Gly Leu Pro Thr Gln Glu
        115                 120                 125

CCA GCA CTG GGG ACC ACC TGC TAC GCC TCA GGC TGG GGC AGC ATC GAA     432
Pro Ala Leu Gly Thr Thr Cys Tyr Ala Ser Gly Trp Gly Ser Ile Glu
    130                 135                 140

CCA GAG GAG TTC TTG CGC CCC AGG AGT CTT CAG TGT GTG AGC CTC CAT     480
Pro Glu Glu Phe Leu Arg Pro Arg Ser Leu Gln Cys Val Ser Leu His
145                 150                 155                 160

CTC CTG TCC AAT GAC ATG TGT GCT AGA GCT TAC TCT GAG AAG GTG ACA     528
Leu Leu Ser Asn Asp Met Cys Ala Arg Ala Tyr Ser Glu Lys Val Thr
                165                 170                 175

GAG TTC ATG TTG TGT GCT GGG CTC TGG ACA GGT GGT AAA GAC ACT TGT     576
Glu Phe Met Leu Cys Ala Gly Leu Trp Thr Gly Gly Lys Asp Thr Cys
```

```
                180                 185                 190
GGG GGT GAT TCT GGG GGT CCA CTT GTC TGT AAT GGT GTG CTT CAA GGT            624
Gly Gly Asp Ser Gly Gly Pro Leu Val Cys Asn Gly Val Leu Gln Gly
        195                 200                 205

ATC ACA TCA TGG GGC CCT GAG CCA TGT GCC CTG CCT GAA AAG CCT GCT            672
Ile Thr Ser Trp Gly Pro Glu Pro Cys Ala Leu Pro Glu Lys Pro Ala
    210                 215                 220

GTG TAC ACC AAG GTG GTG CAT TAC CGG AAG TGG ATC AAG GAC ACC ATC            720
Val Tyr Thr Lys Val Val His Tyr Arg Lys Trp Ile Lys Asp Thr Ile
225                 230                 235                 240

GCA GCC AAC CCC TGAGTGCCCC TGTCCCACCC CTACCTCTAG TAAA                      766
Ala Ala Asn Pro (2) INFORMATION FOR SEQ ID NO:18:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Cys Ala Leu Pro Glu Lys Pro Ala Val Tyr Thr Lys Val Val His Tyr Arg
1               5                   10                  15

Trp Ile Lys Asp Thr Ile Ala Ala Asn
    20                  25

(2) INFORMATION FOR SEQ ID NO:19:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Asp Arg Val Tyr Ile His Pro Phe His Leu Leu Val Tyr Ser
1               5                   10

(2) INFORMATION FOR SEQ ID NO:20:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

(2) INFORMATION FOR SEQ ID NO:21:

(i) SEQUENCE CHARACTERISTICS:
        (A) LENGTH: 18 amino acids
        (B) TYPE: amino acid
        (C) STRANDEDNESS: single
        (D) TOPOLOGY: linear
```

-continued

```
(ii) MOLECULE TYPE: peptide (xi) SEQUENCE DESCRIPTION: SEQ ID NO:21:

Cys Ser Gly Lys Ile Val Ile Ala Arg Tyr Gly Lys Val Phe Arg Gly
1               5                   10                  15

Asn Lys
```

STABLE VARIANT HK2 POLYPEPTIDE

CROSS-REFERENCE TO RELATED APPLICATION

This application is a continuation-in-part of U.S. patent application Ser. No. 08/427,767, filed May 2, 1995 abandoned, which is incorporated by reference herein.

BACKGROUND OF THE INVENTION

The glandular kallikreins are a subgroup of serine proteases which are involved in the post-translational processing of specific polypeptide precursors to their biologically active forms. In humans, three members of this family have been identified, and some of their properties characterized (Clements, *Endoc. Rev.*, 10, 343 (1989); Clements, *Mol. Cell Endo.*, 99, 1 (1994); Jones et al., *Acta Endoc.*, 127, 481 (1992)). The hKLK1 gene encodes the tissue kallikrein protein, hK1, the hKLK2 gene encodes the prostate-specific glandular kallikrein protein, hK2, and the hKLK3 gene encodes the prostate-specific antigen protein, hK3 (PSA). Northern blot analysis of mRNA shows that both hK2 and PSA are expressed mainly in the human prostate, while expression of hK1 is found in the pancreas, submandibular gland, kidney, and other nonprostate tissues (Chapdelaine et al., *FEBS Lett.*, 236, 205 (1988); Young et al., *Biochem.* 31, 818 (1992)).

The nucleotide sequence homology between the exons of hKLK2 and hKLK3 is 80%, whereas the nucleotide sequence homology between the exons of hKLK2 and hKLK1 is 65%. The deduced amino acid sequence homology of hK2 to PSA is 78%, whereas the deduced amino acid sequence homology of hK2 to hK1 is 57%. Moreover, the deduced amino acid sequence of hK2 suggests that hK2 may be a trypsin-like protease, whereas PSA is a chymotrypsin-like protease.

PSA levels are widely used as a prognostic indicator of prostate carcinoma. However, since the concentration of PSA in serum is elevated in patients with either prostatic cancer (pCa) or benign prostatic hyperplasia (BPH), the detection of elevated levels of PSA does not distinguish between these diseases. Moreover, the high degree of homology of hK2 to PSA raises some question as to the specificity of antibodies currently used to detect the levels of PSA. If the levels of circulating hK2 are unrelated to pCa or BPH, then antibodies raised to preparations of PSA which are contaminated with hK2, or to regions of PSA with homology hK2, can result in false positive results. However, determination of the levels of hK2 in serum, and the correlation of those levels in patients with pCa or BPH, have not been accomplished.

Thus, a need exists for a method to isolate and purify hK2 polypeptides for use as therapeutic and/or diagnostic agents.

SUMMARY OF THE INVENTION

The invention provides an isolated, purified variant pre-pro or pro hK2 polypeptide. The term "purified" is to be understood by reference to the procedures described hereinbelow. The variant pre-pro or pro hK2 polypeptide of the invention has at least one amino acid substitution relative to the corresponding wild type hK2 polypeptide. Moreover, the variant pre-pro or pro hK2 polypeptide is more stable to purification than the corresponding wild type hK2 polypeptide. Under the conditions described hereinbelow. A preferred embodiment of the invention includes an isolated homogenous variant hK2 polypeptide having SEQ ID NO:3 or SEQ ID NO:5.

The three dimensional model of hK2 shows that amino acid residue 217 is part of the substrate specificity domain of this protein (Vinhinen, *BBRC*, 204, 1251 (1994); Bridon and Dowell, *Urology*, 45, 801 (1995)). It was surprising and unexpected that a conservative substitution of valine for alanine at this site would generate a more stable form of hK2 which is immunologically similar to wild type hK2. Substitution of other amino acids at position 217 may create a more stable form of hK2. Furthermore, substitution of amino acids at other sites forming the substrate specificity or catalytic domains of hK2 may also lead to a more stable form of the protein. These sites, as predicated by protein modeling, are asp 183, gly 206, ala 217 (substrate specificity domain); ser 189, asp 96, his 41 (catalytic triad); ser 205, trp 204 (main-chain substrate binding residues); and gly 187, asp 188 (oxyanion hole).

Thus, another preferred embodiment of the invention includes an isolated purified variant pre-pro or pro hK2 polypeptide having an amino acid substitution selected from the group consisting of aspartic acid at position 183, glycine at position 206, alanine at position 217, serine at position 189, aspartic acid at position 96, histidine at position 41, serine at position 205, tryptophan at position 204, glycine at position 187, and aspartic acid at position 188.

Further provided is an isolated, purified variant mature hK2 polypeptide having an amino acid substitution selected from the group consisting of aspartic acid at position 183, glycine at position 206, alanine at position 217, serine at position 189, aspartic acid at position 96, histidine at position 41, serine at position 205, tryptophan at position 204, glycine at position 187, and aspartic acid at position 188.

The present invention also provides an isolated nucleic acid molecule encoding a variant pre-pro or pro hK2 polypeptide. The variant pre-pro or pro hK2 polypeptide has at least one amino acid substitution relative to the corresponding wild type pre-pro or pro hK2 polypeptide. Further, the variant pre-pro or pro hK2 polypeptide of the invention is more stable to purification than the corresponding wild type hK2 polypeptide. Another embodiment of the invention includes an isolated nucleic acid molecule encoding a variant pre-pro or pro hK2 polypeptide in which the amino acid substitution is present in the amino acid sequence of the mature form of the variant hK2 polypeptide. A preferred embodiment of the invention includes an isolated nucleic acid molecule having SEQ ID NO:4 or SEQ ID NO:6.

The invention also provides an isolated nucleic acid molecule encoding a variant mature hK2 polypeptide having an amino acid substitution selected from the group consisting of aspartic acid at position 183, glycine at position 206, alanine at position 217, serine at position 189, aspartic acid at position 96, histidine at position 41, serine at position 205, tryptophan at position 204, glycine at position 187, and aspartic acid at position 188. A preferred embodiment of the invention is an isolated nucleic acid molecule encoding a variant mature hK2 polypeptide having SEQ ID NO:1.

The isolated, purified hK2 polypeptides of the invention can be employed as reagents in diagnostic assays to detect the presence of hK2 in samples derived from human tissues or physiological fluids. For example, isolated hK2 can be bound to a detectable label and employed in competitive immunoassays for hK2, as described in U.S. patent application Ser. No. 08/096,946, filed Jul. 22, 1993, now U.S. Pat. No. 5,516,639 the disclosure of which is specifically incorporated by reference herein.

Yet another embodiment of the invention is an immunogenic composition or a vaccine comprising the isolated, purified variant pre-pro, pro or mature hK2 polypeptide of the invention in combination with a pharmaceutically acceptable carrier. The administration of the immunogenic composition or vaccine to an animal induces the production of antibodies that bind the variant hK2 polypeptide.

The present invention further provides an antibody that specifically binds a variant pre-pro or pro hK2 polypeptide of the invention and does not bind hK3. A preferred embodiment of the invention provides an antibody which binds the variant pre-pro or pro hK2 polypeptide of the invention and also binds the mature form of the variant hK2 polypeptide, the mature form of the wild type hK2 polypeptide, or both. Another preferred embodiment of the invention includes an antibody which binds the variant pre-pro or pro hK2 polypeptide of the invention and also binds the pre-pro or pro form of the wild type hK2 polypeptide. Yet a further preferred embodiment of the invention includes an antibody which binds the variant pre-pro or pro hK2 polypeptide of the invention and does not bind the mature form of the variant hK2 polypeptide, the mature form of the wild type hK2 polypeptide, or the mature form of the variant or the wild type hK2 polypeptide.

Yet another embodiment of the invention is an antibody that specifically binds the variant mature hK2 polypeptide of the invention and does not bind hK3. A preferred embodiment of the invention includes an antibody which binds the variant mature hK2 polypeptide of the invention and which also binds the mature form of the wild type hK2 polypeptide. Another preferred embodiment of the invention includes an antibody that specifically binds the variant mature hK2 polypeptide of the invention and which does not bind the pro form the variant hK2 polypeptide or the pro form of the wild type hK2 polypeptide. Yet another preferred embodiment of the invention includes an antibody that specifically binds the variant mature hK2 polypeptide of the invention and which does not bind the pre-pro form the variant hK2 polypeptide or the pre-pro form of the wild type hK2 polypeptide.

Therefore, hK2 polypeptides, as well as variants and subunits thereof, produced by the present method can be used to produce populations of antibodies that, in turn, can be used as the basis for direct or competitive assays to detect and quantify hK2 polypeptides (or "protein") in samples derived from tissues such as prostate carcinomas, cells such as prostate cell lines, or from fluids such as seminal fluid or blood. Thus, the present invention provides populations of monoclonal or polyclonal antibodies that specifically bind to an hK2 polypeptide, while not significantly binding to hK3. The term "significantly" is defined by reference to the comparative assays discussed hereinbelow. These antibodies can be used in affinity chromatography, to purify their hK2 polypeptide binding partners from natural sources.

Further provided is a chimeric expression vector. The chimeric expression vector comprises a nucleic acid molecule encoding the variant pre-pro, pro or mature hK2 polypeptide of the invention operably linked to control sequences recognized by a host cell transformed with the vector.

Also provided is a method of using a nucleic acid molecule encoding a variant hK2 polypeptide. The method comprises expressing the nucleic acid molecule encoding the variant pre-pro, pro or mature hK2 polypeptide of the invention in a cultured host cell. The nucleic acid molecule is operably linked to control sequences recognized by the host cell. The variant hK2 polypeptide is then recovered from the host cell or from the culture media.

Yet another embodiment of the invention is a diagnostic kit for detecting or determining phK2. The kit comprises packaging, containing, separately packaged (a) a solid surface capable of having bound thereto antibodies which bind to at least the pro form of hK2 and not to hK3, and (b) a known amount of an antibody which specifically binds the pro form of hK2 and not hK3 or hK2. The antibody is detectably labeled or binds to a detectable label.

A further embodiment of the invention is a method for detecting or determining phK2 in a sample of a human physiological fluid containing phK2. The method comprises providing an amount of purified antibodies which specifically react with human phK2, wherein said antibodies do not significantly react with hK3 and hK2, and wherein said antibodies are capable of attachment to a solid surface. The antibodies are contacted with the sample to be tested for a sufficient time to allow the formation of binary complexes between at least a portion of said antibodies and a portion of said phK2. Then the presence or amount of phK2 complexed with said antibodies is detected or determined.

hK2 has a trypsin-like activity which is in general agreement with molecular modeling studies (Vinhinen, supra, 1994; Bridon and Dowell, supra, 1995). The enzymatic activity of hK2 is specific for selected arginines and is different from the substrate specificity of trypsin. Thus, it may be possible to generate hK2-specific substrates or inhibitors which in turn could be used in activity-based diagnostic assays to detect hK2 in bodily fluids.

Therefore, the present invention also provides a method of detecting hK2 in vitro. The method comprises contacting a sample comprising an amount of an hK2 polypeptide with an amount of a synthetic peptide substrate for a sufficient time to allow cleavage of the peptide substrate by the hK2 polypeptide. The peptide substrate comprises contiguous amino acid residues which form a site to which hK2 binds. The presence or amount of cleavage of the peptide substrate is then detected or determined.

PSA forms covalently-linked complexes with ACT and MG in human serum (Leinonen et al., *Clin. Chem.*, 34, 2098 (1993)). Monitoring the ratios of different forms of PSA (complexed versus uncomplexed) in serum has been useful in differentiating between BPH and pCa (Christensson et al., *J. Urol.*, 150, 100 (1993)).

The results presented hereinbelow show that hK2 polypeptides also form complexes with ACT and MG. Complex formation of hK2 with ACT was unexpected since ACT is typically an inhibitor of chymotrypsin-like proteases. However, it suggests that hK2 bears conformational/ structural similarities with PSA which dictate its reactivity with inhibitors. hK2 complexed with ACT and MG along with free (unbound) hK2 would thus be expected to represent the major immunologically measurable components of hK2 in human serum. Therefore, monitoring these forms could be important in distinguishing between pCa and BPH.

Thus, a further embodiment of the invention is a method to detect hK2 complex formation with plasma proteins. The method comprises separating, in a sample, hK2 polypeptides which are not bound to plasma proteins from hK2 polypeptides which are bound to plasma proteins. The amount of hK2 polypeptides which are bound to plasma proteins relative to the amount of hK2 polypeptides which are not bound to plasma proteins is then determined.

BRIEF DESCRIPTION OF THE FIGURES

FIG. 1 depicts the amino acid sequences of wild type mature hK2 (SEQ ID NO:12) and hK3 (SEQ ID NO:7).

FIG. 2 depicts the amino acid sequence, and corresponding nucleic acid sequence, of wild type pphK2 (SEQ ID NO:14 and SEQ ID NO:15, respectively), phK2 (SEQ ID NO:16 and SEQ ID NO:17) and hK2 (SEQ ID NO:12 and SEQ ID NO:13). Codon 217 (GCT, Ala) is shown in bold and underlined.

FIG. 8 depicts Western blot analysis of seminal fluid using monoclonal antibody (mAb) hKlG 586.1. Processed seminal fluid was diluted 1:1 in PBS and centrifuged at 10,000 X g for 20 minutes. The supernatant was subjected to SDS/PAGE on a 8–25% gel using the PhastSystem (Pharmacia). Protein was transferred to nitrocellulose and incubated with protein-G purified HK1G 586.1 (1 μg/ml) followed by goat anti-mouse IgG-HRP (1:1000). The blot was developed using the ECL detection system (Amersham).

FIG. 9 represents a blot similar to the blot shown in FIG. 9 but which was probed with HK1G 464.3, which detects phK2 (1:1000), followed by goat anti-mouse IgG-HRP (1:500). The blot was developed with ECL (Amersham) according to the manufacturer's instructions. Purified phK2$^{v217}$ and hK2$^{v217}$ were used as controls. The position of hK2 is indicated by the arrow.

FIG. 10 represents a similar blot probed with HKIG 464.3. Goat anti-mouse IgG-HRP (1:500) was used as a secondary antibody and the blot was developed with ECL (Amersham) according to the manufacturer's instructions. Purified phK2$^{v217}$ and hK2$^{v217}$ were used as controls. The position of hK2 is indicated by the arrow.

FIG. 12 represents a blot probed with HK1G 464.3 as described above. Purified phK2$^{v217}$ and phK2$^{v217}$ were used as controls. The position of hK2 is indicated by an arrow.

FIG. 13 represents a blot probed with HK1G 464.3. Goat anti-mouse IgG-HRP (1:500) was used as a secondary antibody and the blot was developed with ECL (Amersham) according to manufacturer's instructions. Purified phK2$^{v217}$ and hK2$^{v217}$ were used as controls. The position of hK2 is indicated by an arrow.

FIG. 14 represents a blot which was probed with HK1G 464.3. Goat anti-mouse IgG-HRP (1:500) was used as a secondary antibody and the blot was developed with ECL (Amersham) according to manufacturer's instructions. Purified phK2$^{v217}$ and hK2$^{v217}$ were used as controls. The position of hK2 is indicated by an arrow.

FIG. 16 depicts the specificity of hK2 and PSA for different peptide substrates. Open arrows denote peptide bonds cleaved by PSA; solid arrows denote bonds cleaved by hK2. Peptide #1 represents amino acid residues 210–236 of hK2 SEQ ID NO:18. Peptide #2 represents amino acid residues 1–14 of angiotensinogen, i.e., the renin substrate tetradecapeptide SEQ ID NO:19. Peptide #3 represents amino acid residues −7 to +7 of phK2 SEQ ID NO:14. Peptide #4 represents amino acid residues 41–56 of hK2 SEQ ID NO:12. Peptide #5 represents the amino acid sequence of the oxidized beta chain of insulin SEQ ID NO:20. Peptide #6 represents amino acid residues 196–213 of PMSA SEQ ID NO:21.

DETAILED DESCRIPTION OF THE INVENTION

Figure 3:
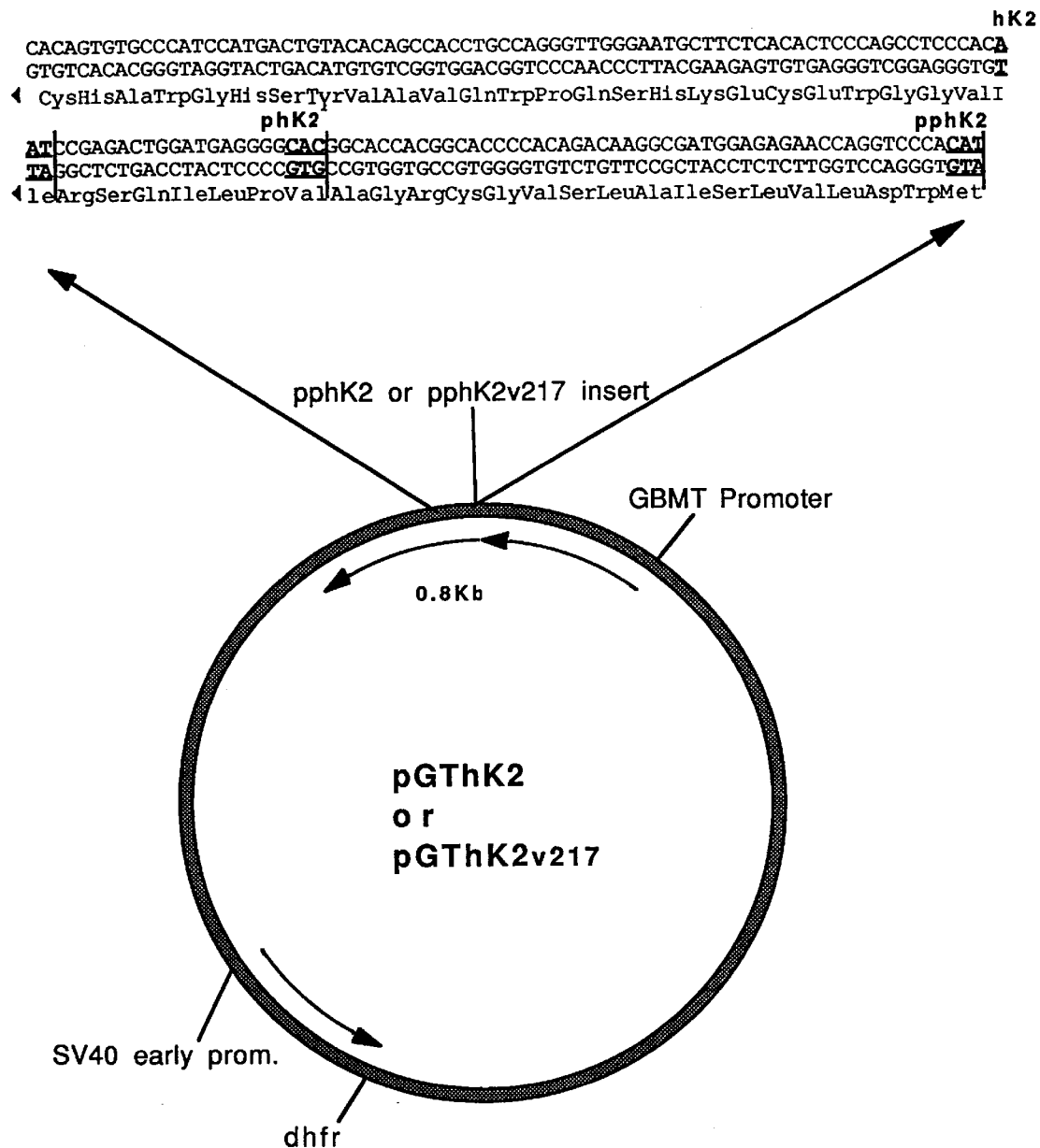
FIG. 3 is a schematic diagram of the pGT expression vectors pGThK2 and pGThK2$^{v217}$.

The high degree of amino acid sequence homology of hK2 to PSA, and the fact that the expression of both hK2 and PSA is essentially limited to the prostate, suggests that measuring the serum concentrations of both proteins can be useful in the diagnosis and monitoring of prostatic cancer (pCa). Recently, pphK2 was expressed in bacteria (Saedi et al., *Mol. Cell. Endoc.*, 109, 237 (1995)). Bacterially derived pphK2 can be used to generate antibodies to the non-conformationally dependent epitopes on hK2. However, to discern the steps involved in the biosynthesis of hK2 and to obtain antibodies specific for the fully processed and secreted form of hK2, expression of hK2 in mammalian cells is necessary.

As used herein, the term "hK2 polypeptide" includes recombinant pre-pro, pro and mature hK2 polypeptides. A mature hK2 polypeptide having the amino acid sequence shown in FIG. 1 (SEQ ID NO:12), as well as "variant" polypeptides which share at least 90% homology with SEQ ID NO:12 in the regions which are substantially homologous with hK3, i.e., which regions are not identified by bars as shown in FIG. 1. Such hK2 polypeptides also possess antigenic function in common with the mature hK2 molecule of FIG. 1, in that said polypeptides are also definable by antibodies which bind specifically thereto, but which do not cross-react with hK3 (or hK1). Preferably, said antibodies react with antigenic sites or epitopes that are also present on the mature hK2 molecule of FIG. 1. Antibodies useful to define common antigenic function are described in detail in Ser. No. 08/096,946, now U.S. Pat. No. 5,516,639 i.e., polyclonal antisera prepared in vivo against hK2 subunit 41–56.

"Isolated hK2 nucleic acid" is RNA or DNA containing greater than 15, preferably 20 or more, sequential nucleotide bases that encode a biologically active hK2 polypeptide or a variant fragment thereof, that is complementary to the non-coding strand of the native hK2 polypeptide RNA or DNA, or hybridizes to said RNA or DNA and remains stably bound under stringent conditions. Thus, the RNA or DNA is isolated in that it is free from at least one contaminating nucleic acid with which it is normally associated in the natural source of the nucleic acid and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated hK2 nucleic acid is RNA or DNA that encodes a biologically active hK2 polypeptide sharing at least 90% sequence identity with the hK3-homologous regions of the hK2 peptide of FIG. 1, as described above. The term "isolated, substantially homogenous" as used with respect to an hK2 polypeptide is defined in terms of the methodologies discussed herein below.

As used herein, the term "recombinant nucleic acid," i.e., "recombinant DNA" refers to a nucleic acid, i.e., to DNA that has been derived or isolated from any appropriate tissue source, that may be subsequently chemically altered in vitro, and later introduced into target host cells, such as cells derived from animal, plant, insect, yeast, fungal or bacterial sources. An example of recombinant DNA "derived" from a source, would be a DNA sequence that is identified as a useful fragment encoding hK2, or a fragment or variant thereof, and which is then chemically synthesized in essentially pure form. An example of such DNA "isolated" from a source would be a useful DNA sequence that is excised or removed from said source by chemical means, e.g, by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome of the host target cell which is the recipient of the DNA, or it is resident in the genome but is not expressed, or not highly expressed.

As used herein, "chimeric" means that a vector comprises DNA from at least two different species, or comprises DNA from the same species, which is linked or associated in a manner which does not occur in the "native" or wild type of the species.

The recombinant DNA sequence, used for transformation herein, may be circular or linear, double-stranded or single-stranded. Generally, the DNA sequence is in the form of chimeric DNA, such as plasmid DNA, that can also contain coding regions flanked by control sequences which promote the expression of the recombinant DNA present in the resultant cell line. For example, the recombinant DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements). Aside from recombinant DNA sequences that serve as transcription units for hK2 or portions thereof, a portion of the recombinant DNA may be untranscribed, serving a regulatory or a structural function.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

Aside from recombinant DNA sequences that serve as transcription units for hK2 or portions thereof, a portion of the recombinant DNA may be untranscribed, serving a regulatory or a structural function.

The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like.

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly Photinus pyralis. Expression of the reporter gene is assayed at a suitable time after the DNA has been introduced into the recipient cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

The recombinant DNA can be readily introduced into the target cells by transfection with an expression vector comprising cDNA encoding hK2, for example, by the modified calcium phosphate precipitation procedure of C. Chen et al., *Mol. Cell. Biol.*, 7, 2745 (1987). Transfection can also be accomplished by lipofectin, using commercially available kits, e.g., provided by BRL.

Suitable host cells for the expression of hK2 polypeptide are derived from multicellular organisms. Such host cells are capable of complex processing and glycosylation activities. In principle, any higher eukaryotic cell culture can be employed in the practice of the invention, whether from vertebrate or invertebrate culture. Examples of invertebrate cells include plant and insect cells. Numerous baculoviral strains and variants and corresponding permissive insect host cells from hosts such as Spodopterafrugiperda (caterpillar), Aedes aegypti (mosquito), Aedes albopictus (mosquito), Drosophila melanogaster (fruitfly), and Bombyx mori have been identified. See, e.g., Luckow et al., *Bio/Technology*, 6, 47 (1988); Miller et al., in *Genetic*

*Engineering*, J. K. Setlow et al., eds., Vol. 8 (Plenum Publishing, 1986), pp. 277–279; and Maeda et al., *Nature*, 315, 592 (1985). A variety of viral strains for transfection are publicly available, e.g., the L-1 variant of Autographa californica NPV and the Bm-5 strain of Bombyx mori NPV, and such viruses may be used, preferably for transfection of Spodopterafrugiperda cells.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. For example, see Lawn et al., *Nucleic Acids Res.*, 2, 6103 (1981), and Goeddel et al., *Nucleic Acids Res.*, 8, 4057 (1980).

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, N.Y., 1989).

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/ 0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

When hK2 polypeptide is expressed in a recombinant cell other than one of human origin, the hK2 polypeptide is completely free of proteins or polypeptides of human origin. However, it is necessary to purify hK2 polypeptide from recombinant cell proteins or polypeptides to obtain preparations that are substantially homogeneous as to hK2 polypeptide. For example, the culture medium or lysate can be centrifuged to remove particulate cell debris. The membrane and soluble protein fractions are then separated. The hK2 polypeptide may then be purified from the soluble protein fraction and, if necessary, from the membrane fraction of the culture lysate. hK2 polypeptide can then be purified from contaminant soluble proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated from the resulting transgenic host cells, derivatives and variants of the hK2 polypeptide can be readily prepared. For example, amides of the hK2 polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the hK2 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. In addition, the internal hK2 amino acid sequence of FIG. 1 can be modified by substituting one or two conservative amino acid substitutions for the positions specified, including substitutions which utilize the D rather than L form. The invention is also directed to variant or modified forms of the hK2 polypeptide. One or more of the residues of this polypeptide can be altered, so long as antigenic function is retained. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

Once isolated, hK2 polypeptide and its antigenically active variants, derivatives and fragments thereof can be used in assays for hK2 in samples derived from biological materials suspected of containing hK2 or anti-hK2 antibodies, as disclosed in detail in Ser. No. 08/096,946 now U.S. Pat. No. 5,516,639. For example, the hK2 polypeptide can be labelled with a detectable label, such as via one or more radiolabeled peptidyl residues, and can be used to compete with endogenous hK2 for binding to anti-hK2 antibodies, i.e., as a "capture antigen" to bind to anti-hK2 antibodies in a sample of a physiological fluid, via various competitive immunoassay format for hK2 which uses anti-hK2 antibodies which are capable of immobilization is carried out by:

(a) providing an amount of anti-hK2 antibodies which are capable of attachment to a solid surface;

(b) mixing a sample of physiological fluid, which comprises hK2, with a known amount of hK2 polypeptide which comprises a detectable label, to produce a mixed sample;

(c) contacting said antibodies with said mixed sample for a sufficient time to allow immunological reactions to occur between said antibodies and said hK2 to form an antibody-hK2 complex, and between said antibodies and said labelled polypeptide to form an antibody-labeled polypeptide complex;

(d) separating the antibodies which are bound to hK2 and antibodies bound to the labeled polypeptide from the mixed sample;

(e) detecting or determining the presence or amount of labelled polypeptide either bound to the antibodies on the solid surface or remaining in the mixed sample; and (f) determining from the result in step (e) the presence or amount of said hK2 in said sample.

In another format which can detect endogenous hK2 in a sample by a competitive inhibition immunoassay, a known amount of anti-hK2 antibody is added to a sample containing an unknown amount of endogenous hK2. The known amount is selected to be less than the amount required to complex all of the hK2 suspected to be present, e.g., that would be present in a sample of the same amount of physiological fluid obtained from a patient known to be prostate cancer. Next, a known amount of the hK2 polypeptide of the invention or a subunit thereof, comprising a detectable label is added. If endogenous hK2 is present in the sample, fewer antibodies will be available to bind the labelled hK2 polypeptide, and it will remain free in solution. If no endogenous hK2 is present, the added labelled polypeptide will complex with the added anti-hK2 antibodies to form binary complexes. Next, the binary antibody-antigen complexes are precipitated by an anti-mammal IgG antibody (sheep, goat, mouse, etc.). The amount of radioactivity or other label in the precipitate (a ternary complex) is inversely proportional to the amount of endogenous hK2 that is present in the sample, e.g., a pellet containing reduced amounts of radioactivity is indicative of the presence of endogenous hK2.

Alternatively to the conventional techniques for preparing polyclonal antibodies or antisera in laboratory and farm animals, monoclonal antibodies against hK2 polypeptide can be prepared using known hybridoma cell culture techniques. In general, this method involves prepared an antibody-producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the f(ab) fragment, as are partially humanized monoclonal antibodies.

The invention will be further described by reference to the following detailed examples.

EXAMPLE 1

Materials and Methods
Construction of Mammalian hK2 Expression Vectors

A cDNA (approximately 820 bp long) encoding the entire prepro-hK2 (pphK2) (from nucleotide #40 to #858 relative to the start site of the pphK2 transcript), as shown in FIG. 2, was synthesized from RNA of human BPH tissue using reverse-transcription polymerase chain reaction (RT-PCR) technology with a pair of hK2 specific oligonucleotide primers (5'ACGCGGATCCAGCATGTGGGACCTGGT TCTCT3'SEQ ID NO:8 and 5'ACAGCTGCAGTTTACTA-GAGGTAGGGGTGGGAC 3'SEQ ID NO:9). This cDNA was generated such that 5' and 3' ends (with respect to pphK2 sense sequence) were bracketed with BamH1 and Pst1 sequences, respectively. The cDNA was then purified by agarose gel electrophoresis, and digested with BamH1 and Pst1 restriction enzymes. The restricted cDNA was ligated with BamH1-Pst1 digested pVL1393 plasmid vector and transformed into the *E. coli* HB101 strain. *E. coli* harboring pphK2 cDNA/pVL1393 plasmid vector were selected. The pphK2 containing insert was sequenced. Plasmid pphK2 cDNA/pVL1393 was mass-produced in *E. coli* and purified by CsCl gradient ultra-centrifugation.

Plasmid pphK2/pVL1393 in *E. coli* HB101 has been deposited in the American Type Culture Collection, Rockville, Md., USA on May 2, 1994 under the provisions of the Budapest Treaty and has been assigned accession number ATCC 69614.

A 0.8 kb fragment representing the entire pphK2 coding sequence (FIG. 2) was generated by PCR using primers A (5'ATATGGATCCATATGTCAGCATGTGGGACCTGG TTCTCTCCA3') (SEQ ID NO:10) and B (5'ATATGGATCCTCAGGGGTTGGCTGCGATGGT3') (SEQ ID NO:11) and plasmid pVL1393 containing pphK2 (gift from Dr. Young, Mayo Clinic) as the template. PCR products were inserted into the TA-cloning vector (Invitrogen Corp., San Diego, Calif.) and the DNA of the entire insert was sequenced.

To obtain the mammalian hK2 expression vectors, the hK2-containing inserts were isolated from the corresponding TA clones and inserted into the Bc11 site of the plasmid pGT-d (Berg et al., *Nucl. Acids Res.*, 20, 54–85 (1992)) (gift from Dr. Brian Grinnell, Lilly) under the control of the GBMT promoter. The mammalian expression vectors, PLNS-hK2 and PLNC-hK2 were obtained by cloning the 0.8 kb wild type hK2 insert from the corresponding TA vector into the plasmids, PLNSX and PLNCX (Miller et al., *Biotech.*, 7, 980 (1989)), respectively. The orientation of the insert in all the mammalian expression vectors was confirmed by DNA sequencing.

Generation of Recombinant Clones

AV12–664 (ATCC CRL-9595), a cell line derived from adenovirus-induced tumors in Syrian hamster, and DU145 cells were cultured in Dulbecco's modified Eagle's medium (high glucose) supplemented with 10% fetal bovine serum (D10F). PC3 cells were cultured in Minimal Eagle Medium containing 10% fetal bovine serum. AV12 cells were transfected with the hK2 expression vectors using the calcium phosphate method (Maniatis et al., supra (1989)). Three days after transfection cells were resuspended in D10F+200 nM methotrexate (MTX). Drug-resistant clonal cell lines were isolated after 2–3 weeks and their spent medium was analyzed by Western blots. PC3 and DU145 cells were transfected with hK2 mammalian expression vectors using lipofectamine (Gibco-BRL, Gaithersburg, Md.) and clones (PC3-hK2 and DU145-hK2) were selected in media containing 400 μg/ml G418.

Purification and Sequencing of the Protein

AV12-hK2 clones were grown in D10F+200 nM MTX. At about 60% confluency the cells were washed with Hank's balanced salt solution and resuspended in serum-free HH4 medium. The spent medium was collected 7 days after the addition of serum-free spent medium and stored at −20° C. To purify the protein, the serum-free spent medium was concentrated and exchanged into 50 mM sodium bicarbonate pH 8. Samples were filtered with 0.2 μ filters and then pumped directly onto a TSK DEAE-5PW HPLC column, 21 mm X 150 mm, at a flow rate of 5 ml/minute. Buffer A contained 50 mM Na bicarbonate pH 7.9 and Buffer B contained 50 mM Na bicarbonate plus 0.5 M NaCl pH 7.6. The elution profile was developed with a gradient from 0–50% Buffer B over 35 minutes; 50–100% B from 35–40 minutes and isocratic elution at 100% B for 5 minutes before re-equilibration in Buffer A. The flow rate was 5 mL/minute throughout. In the above procedure, borate buffer could replace bicarbonate buffer with no noticeable difference.

DEAE fractions were assayed for the presence of hK2 by the dried-down ELISA method (see below) using rabbit anti-pphK2 (Saedi et al., *Mol. Cell. Endoc.*, 109, 237 (1995)). Fractions with hK2 activity were pooled and concentrated by ultrafiltration with membranes (10 kD cut off) to approximately 5–8 mL. Solid ammonium sulfate was then added to a final concentration of 1.2 M. This sample was then injected onto a PolyLC, polypropyl aspartamide column, 1000 Å pore size, 4.6 mm X 200 mm, to resolve proteins by hydrophobic interaction chromatography (HIC). Buffer A was 20 mM Na phosphate, 1.2 M Na sulfate pH 6.3 and Buffer B was 50 mM Na phosphate, 5% 2-propanol, pH 7.4. The elution gradient was 0–20% B over 5 minutes; 20–55% B from 5–20 minutes, isocratic at 55% B from 20–23 minutes, 55–100% B from 23–25 minutes; isocratic at 100% B for 2 minutes before re-equilibration Buffer A. The flow rate was 1 mL/minute. The HIC peak containing hK2 which eluted at about 50% B was exchanged into 50 mM borate buffer pH 8 by repeated concentration with Centricon-10 (Amicon) 10 K MW cutoff ultrafiltration. Purity was assessed by both SDS-PAGE and Western blot analyses. The extinction coefficient used to estimate hK2$^{v217}$ concentrations was $A_{280}$ of 1.84=1 mg/ml.

In some cases the HIC peak containing hK2 was purified further by size exclusion chromatography (SEC) on a 10/30 Pharmacia S12 column. In this case the HIC peak containing hK2 was concentrated by ultrafiltration as above to less than 1 mL and then applied to the size exclusion column equilibrated in 100 mM ammonium acetate pH 7 or sodium borate pH 8. The flow rate was 0.7 mL/minute. The hK2 peak was then concentrated by ultrafiltration. The peak collected off SEC in ammonium acetate was lyophilized to remove the buffer and then was reconstituted in water. An aliquot of this sample was hydrolyzed in gaseous 6 N HCl under vacuum for 20 hours at 112° C. then reconstituted in 0.1 N HCl and analyzed on a Hewlett Packard Aminoquant amino acid analyzer utilizing pre-column derivatization of amino acids with OPA for primary and FMOC for secondary amines.

A HK1G 586.1 affinity resin was used to purify hK2 by affinity chromatography. HK1G 586.1 monoclonal antibody (mAb) was coupled with Pharmacia GammaBind plus Sepharose (cat. no. 17–0886) according to Schneider (*J. Biol. Chem.*, 257, 10766 (1982)). Briefly, HK1G 586.1 mAb and resin were incubated overnight at 4° C. with rotation. Resin was centrifuged (500 X g for 5 minutes at 4° C.) and washed twice with 0.2 M triethanolamine, pH 8.2. Amine groups were cross-linked in fresh cross linker solution (25 mM dimethyl pimelimidate dihydrochloride in 0.2 M triethanolamine, pH 8.2) for 45 minutes at room temperature (22° C.). The resin was quenched with 20 mM ethanolamine, pH 8.2, for 5 minutes at room temperature and then washed twice with 1 M NaCl, 0.1 M $PO_4$, pH 7.0. The resin was washed two more times with PBS and stored at 4° C. with 0.05% NaN3 until use.

An Applied Biosystems Model 477a pulsed liquid phase sequencer was used to sequence the proteins and the peptides. The Model 477a employs automated Edman degradation chemistry to sequentially release amino acids from the N-terminus followed by PTH derivatization and chromatography by reversed-phase HPLC. The peptide samples were applied to the sequencer on biobrene-treated glass fiber filter supports and whole proteins were applied either to biobrene-treated filters or to pre-activated Porton filters (Beckman, Fullerton, Calif.). Samples sequenced off blots were first run as mini-gels on the Novex system (Novex, San Diego, Calif.) then transferred to Problot PVDF membrane, visualized with Commassie blue, the appropriate band cut out and sequenced directly from the PVDF membrane.

Monoclonal Antibody Production

A/J mice were injected with 50 μl of phK2 in complete Freund's adjuvant (CFA) i.p. on day 1,25 μg of phK2 in incomplete Freund's adjuvant (IFA) i.p. on day 14 and 25 μg phK2 in PBS i.p. on day 28. Three days prior to fusion, mice were boosted with 10 μg of phK2 in PBS i.v. Mice were sacrificed and a single cell suspension was prepared from the spleens. Immune B cells were fused with P3.653 myeloma cells using techniques well known to the art. Clones were screened by ELISA and selected based on the reactivity of supernatants to hk2$^{v217}$ and phK2$^{v217}$ and minimal reactivity with PSA. Two clones selected by these criteria, clones HK1G464 and HK1G586, were subcloned using FACStar plus cell sorter to deposit single cells onto mouse spleen feeder layers. Subdlones HK1G464.3 and HK1G586.1 were used for further studies.

Another fusion, which employed the same protocol described above except that the immunogen was hK2$^{v217}$, alum was used instead of CFA and IFA, BALB/c mice were used instead of A/J mice, produced clone HK1H247.

ELISA Assays

A dried-down ELISA format was used to measure hK2 in the serum-free spent medium of the clones and in the fractions collected during hK2 purification. Microtiter plates (Becton Dickinson Labware, N.J.) were coated with 50 μl of spent media or column fractions overnight at 37° C. The wells were washed with PBS+0.1% Tween 20 (PBST) and incubated for one hour with 50 μl of primary antibodies. The wells were washed again with PBS+T and incubated for one hour at 37° C. with 50 μl of goat anti mouse-IgG or goat anti rabbit-IgG Fc antibodies coupled with horseradish peroxidase (1:500, Jackson Immunosearch Laboratories, Inc., West Grove, Pa.). The wells were washed with PBST, incubated with o-phenylenediamine dihydrochloride (OPD, Sigma, Mo.) for 5 minutes, and the colorimetric reaction was measured at $A_{490}$ with an ELISA reader (Biotek Instruments, Inc., model EL310, VT). All samples were assayed in duplicate. The serum-free spent medium from AV12 cells transfected with vector alone was used as negative control.

Antibodies were tested in a solution-based ELISA format using biotinylated phK2$^{v217}$, hK2$^{v217}$, and PSA. PSA was purified by the method of Sensabaugh and Blake (*J. Urology*, 144, 1523 (1990)). Twenty ng of biotinylated hK2$^{v217}$ or phK2$^{v217}$ diluted in 50 µl Buffer A (8.82 mM citric acid, 82.1 mM sodium phosphate (dibasic), 10% BSA, 0.1% mannitol, 0.1% Nonidet P-40, pH 7.0) or 0.25 ng biotinylated PSA diluted in 10% horse serum (HS) in PBS was incubated with 50 µl of hybridoma supernatants, negative control supernatants (i.e., irrelevant hybridoma supernatant for phK2$^{v217}$ and hK2$^{v217}$, or 20 µg/ml irrelevant purified mAb in HS for PSA), or positive control supernatants (i.e., 20 µg/ml purified PSM773 (anti-PSA) mAb in HS for PSA, or HK1D 104 (anti "hK2") hybridoma supernatant for phK2$^{v217}$ and hK2$^{v217}$). HCO514, a mAb against hCG, was used as a negative control in PSA assays, and ZTG085, a mAb against the tau, was used as a negative control in hK2 assays.

These mixtures of antibodies and antigens were allowed to incubate for 1 hour with shaking in a streptavidin coated microtiter plate (Labsystems, Helsinki, Finland). The plate was washed 3 times with 300 µl of PBS, 0.1% Tween-20 (PBST), and incubated with 100 µl of gamma-specific goat anti mouse IgG-horseradish peroxidase conjugate (Jackson ImmunoResearch Laboratories, Inc., Westgrove, Pa.), diluted 1: 10,000 in HS, with shaking for 1 hour. After a second PBST washing, color was developed for 30 minutes, with shaking, following the addition of 100 µl of 1 mg/ml o-phenylenediamine in 50 mM phosphate-citrate buffer, 0.03% sodium perborate, pH 5.0 (Sigma Chemical, St. Louis, Mo.). The reaction was quenched by the addition of 50 µl 4 N $H_2SO_4$. The color intensity was determined by measuring the absorbance at 490 nm and 540 nm using a microtiter plate reader. Absorbances above 2.6 at 490 nm were corrected with 540 nm reading. Sample values are averages ± standard deviation of triplicates. Control values are averages of duplicates.

Western Blot Assays

Western blot analyses were performed using standard procedures. Serum-free spent media were concentrated ten fold using Centricon 10 (Amicon, Inc., Beverly, Mass.) and subjected to SDS/PAGE using a 12% gel (Bio-Rad, Inc., Melville, N.Y.). For analytical purposes, SDS/PAGE was performed on a Pharmacia PhastSystem using 8–25% gradient gels. After electrophoresis, proteins were transferred onto nitrocellulose membrane and blocked overnight at 4° C. with 2% nonfat dried milk in PBS. Blots were rinsed then incubated with primary antibody (1:1000 dilution of ascites, or 1 µg/ml of purified mAbs or polyclonal Abs) for 1 hour at 22° C. Blots were then washed and incubated for 45 minutes with secondary antibody (Goat anti-mouse-HRP or goat anti-rabbit-HRP, 1:500, Jackson Immunosearch Laboratories, Inc., West Grove, Pa.). The immunoreactive bands were detected by developing the blot using DAB (Sigma, St. Louis, Mo.) plus $H_2O_2$ or by using the ECL (Amersham, Buckinghamshire, England) system according to manufacturer's instructions.

Covalent Complex Formation

To test for covalent complex formation, 0.175 µM hK2 was incubated with 20 µM inhibitor at pH 8 in 100 mM borate buffer. Inhibitors tested were 1-antichymotrypsin, 1-antitrypsin, 1-antiplasmin, antithrombin and 2-macrogobulin. To 5 µl of hK2 (10 µg/ml) was added the calculated µg of inhibitor prepared in 100 mM borate buffer and, if needed, each sample brought up to a total volume of 10 µl. Samples were incubated for 3 hours at 37° C. whereupon 1.5 µl of 7 X PhastSystem SDS sample buffer containing 35% 2-mercaptoethanol was added and the sample boiled for 3 minutes in a water bath. Samples were diluted ¼ in SDS sample buffer prior to application to SDS/PAGE and Western analyses.

Proteolysis of Peptide Substrates

To determine the ability of hK2 to cleave peptide substrates, peptides were dissolved in DMSO at 10 mg/ml then diluted 1:10 into 100 mM borate buffer pH 8 containing PSA, hK2 or trypsin. Typical experiments were performed as follows: 1 µl of peptide was added to 7 µl of 100 mM borate buffer and then 2 µl of hK2 (10 µg/ml), PSA (500 µg/ml) or trypsin (0.5 µg/ml) were added. In general, samples were incubated for 16 hours at 37° C. Samples were quenched with 100 µl of 0.2% TFA/water and the quenched sample was applied directly to a Vydac C-18 reversed-phase column attached to a BioRad Model 800 HPLC equipped with an AS100 autosampler, dual 1350 pumps and Biodimension scanning UV-VIS detector. Solvent A was 0.1% TFA/water and Solvent B was acetonitrile containing 0.1% TFA. The sample was applied in 90% solvent A and the gradient developed to 60% solvent B in 10 minutes. Absorbance was monitored simultaneously at 220 nm and 280 nm. Peaks collected off HPLC were concentrated by vacuum centrifugation or lyophilization and then applied to the amino acid sequencer to identify individual fragments. In some cases 10 µl of the quenched sample mixture was applied directly to the sequencing membrane and, since the sequence was known, the cleavage sites were determined from the distribution of amino acids present in each cycle.

Protease Assays using Chromogenic Substrates

Assays to measure the hydrolysis of para-nitroanalide derivatized substrates were performed using an HP 8452A UV-VIS spectrophotometer equipped with a programmable, thermostated 7-position cell holder. Assays were performed in 100 mM sodium borate pH 8 incubated at 37° C., the absorbance increase monitored at 405 nm. Methoxysuccinyl-Arg-Pro-Tyr-para-nitroanilide (MeO-Suc-R-P-Y-pNA) and H-D-pro-phe-arg-para-nitroanilide (P-F-R-pNA) were 1 mM in the assay.

An ABI model 431A peptide synthesizer using standard FastMoc chemistry was employed to synthesize all of the peptides listed in FIG. 16 except #2, angiotensinogen and #5, oxidized beta-chain of insulin which were obtained from Sigma. The mass of each synthesized peptide was confirmed by mass spectrometry (University of Michigan, Core Facility) using ES/MS. An ABI Model 477a sequencer described above was employed to confirm peptide sequence.

Conversion of phK2$^{v217}$ to hK2$^{v217}$

Figure 17A:
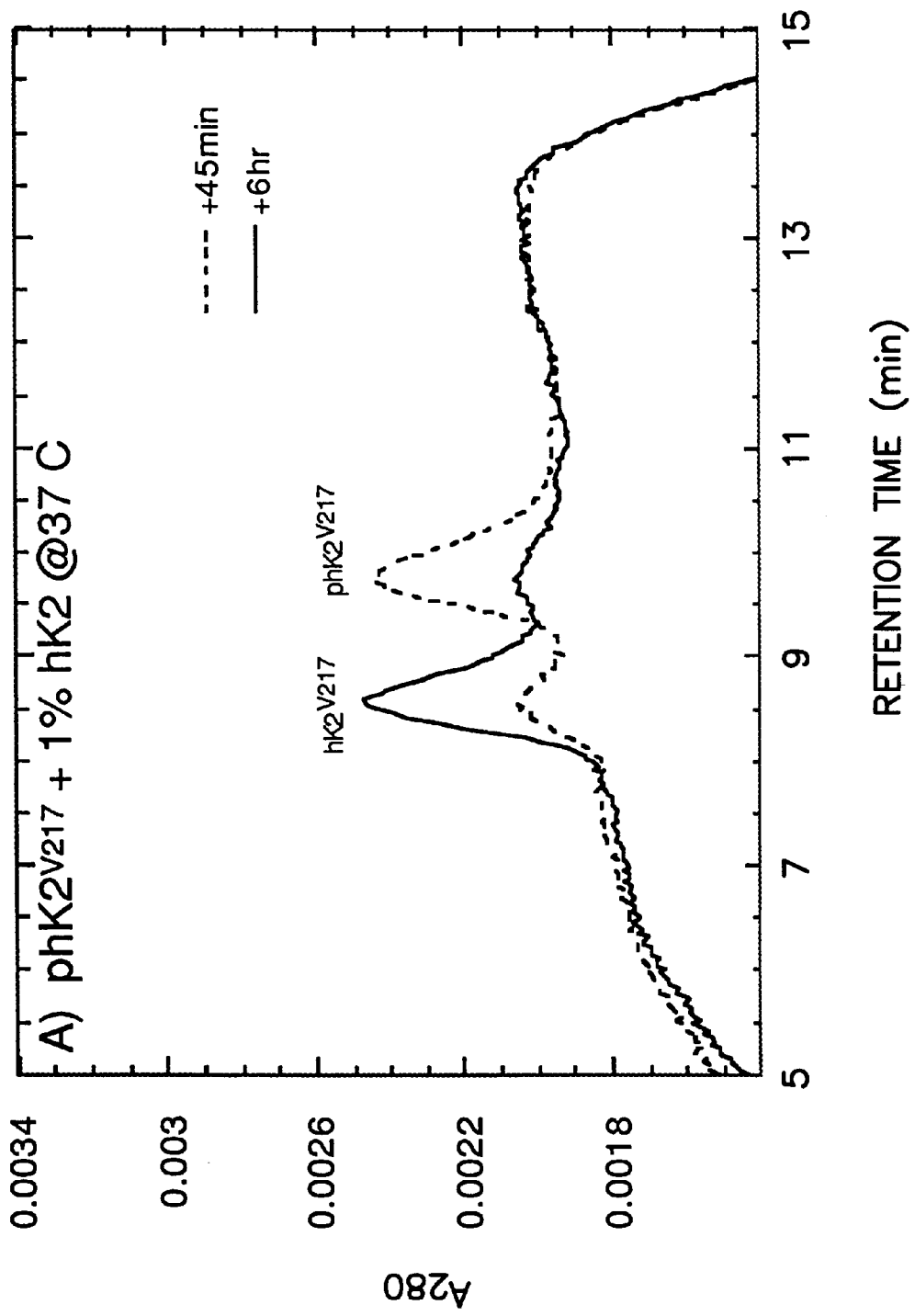
FIGS. 17A–B depicts the activation of phK2$^{v217}$ by hK2 but not hK2$^{v217}$. phK2$^{v217}$ contains the pro leader peptide sequence VPLIQSR, a sequence not present in hK2$^{v217}$. Panel A shows phK2$^{v217}$ incubated with 1% w/w hK2. Panel B is a control with 40% w/w hK2$^{v217}$ incubated with phK2$^{v217}$ for 6 hours.
Figure 17B:
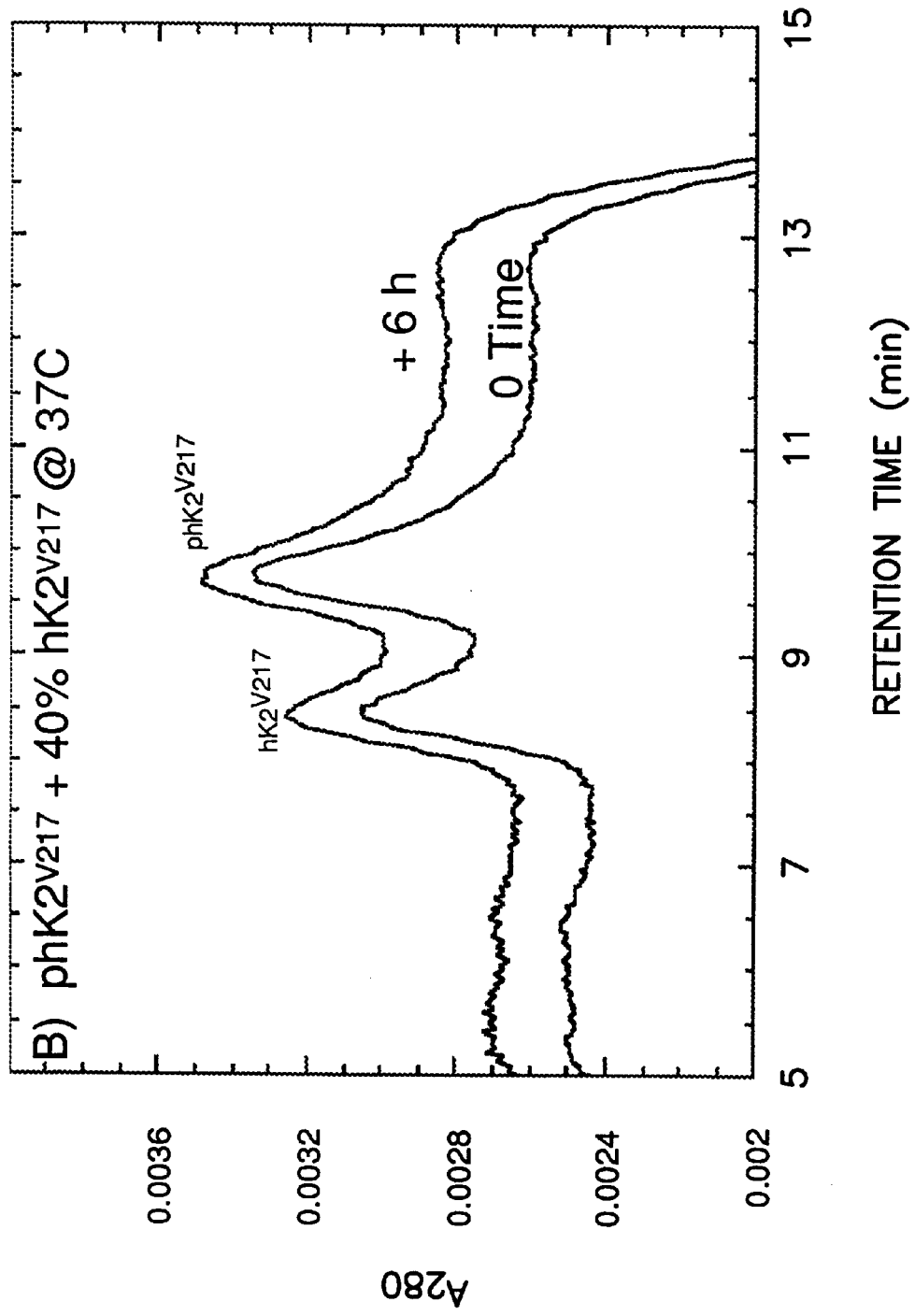

Samples of phK2$^{v217}$ at 100–400 µg/ml in 50 mM sodium borate were incubated with 1% w/w trypsin or hK2 at 37° C. The conversion of pro to mature was monitored by dilution of 1–2 µg of hK2$^{v217}$ starting material into 100 µl HIC Buffer A and resolution of the two forms by HIC-HPLC as described above. The incubation of hK2$^{v217}$ with phK2$^{v217}$ was conducted in the same manner except that comparable amounts of the two forms were incubated together as seen in FIG. 17B.

EXAMPLE 2

Expression and Purification of hK2$^{v217}$ in Mammalian Cells

To express hK2 in mammalian cell lines, a 0.8 kb fragment encoding the entire coding sequence of hK2 (pphK2) (FIG. 2) was amplified using PCR, subcloned into the vector PCR II (TA) and several clones were isolated. The nucleotide sequence of the entire pphK2 insert in a few of these clones was determined to detect any mutations that may have been caused by PCR amplification. Two clones, one having a wild type hK2 insert, TA-hK2, and one having a mutant hK2 insert, TA-hK2$^{v217}$, were selected for further analysis. TA-hK2$^{v217}$ contains a substitution of T for C at codon 650 of hK2 resulting in a conservative substitution of valine (GTT) for alanine (GCT) at amino acid residue 217 of hK2 (FIG. 2). To obtain mammalian expression vectors, pphK2 inserts of TA-hK2 and TA-hK2$^{v217}$ were subcloned into plasmid PGT-d under the control of the GBMT promoter resulting in plasmids pGThK2 and pGThK2$^{v217}$ (FIG. 3). The GBMT promoter is composed of several regulatory sequences and is activated by the adenovirus E1a protein(s) (Berg et al., supra (1992)).

To determine whether the product of the pphK2$^{v217}$ gene would be expressed in mammalian cells, the plasmid pGThK2$^{v217}$ was transfected into AV12–664 cells. This cell line is derived from a tumor induced in Syrian hamster by adenovirus type 12 and expresses the adenovirus E1a protein. The E1a protein activates the GBMT promoter which results in the expression of the gene product under the control of this promoter. After 2–3 weeks, MTX-resistant clonal cells were isolated and their spent medium were analyzed by Western blots. Several clones were identified which secreted into the media a polypeptide immunoreactive to anti-pphK2 antiserum. One clone (AV12-pGThK2$^{v217}$ #2) was selected for further characterization and protein purification.

Figure 4A:
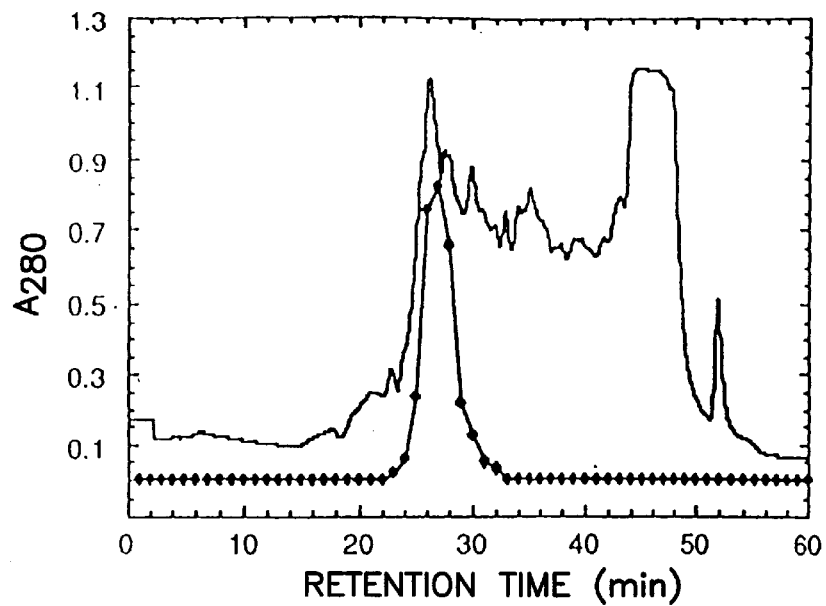
FIG. 4(A) depicts a DEAE chromatogram of 7 day spent medium from AV12 cells transfected with a vector encoding pphK2$^{v217}$. A sample of the spent medium was applied in bicarbonate buffer, pH 8 and eluted with a salt gradient. The $A_{280}$ elution profile is represented by a solid line. The dotted line represents the results of an ELISA assay of a portion of individual column fractions which was dried onto microtiter plates and developed with a rabbit anti-pphK2 antibody.
Figure 4B:
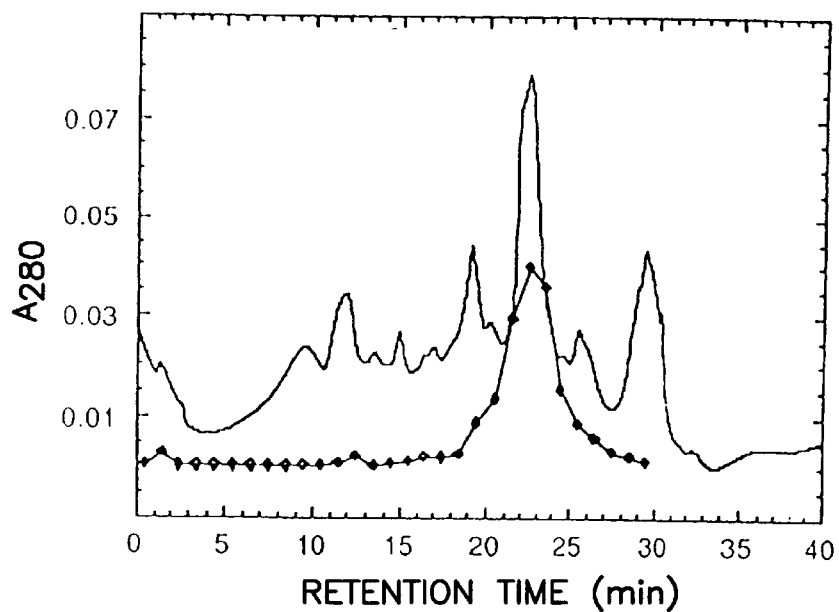
FIG. 4(B) depicts the hydrophobic interaction profile of pooled DEAE fractions. Fractions 24 to 30 from the DEAE chromatographic eluates of (A) were pooled, concentrated and applied to an HIC (hydrophobic interaction chromatography) column in 1.2 M sodium sulfate, and eluted with a decreasing salt gradient. The elution profile ($A_{280}$) is represented by a solid line. The dotted line represents the results of an ELISA assay of a portion of individual column fractions which was dried onto microtiter plates and developed with a rabbit anti-hK2 antibody.
Figure 4C:
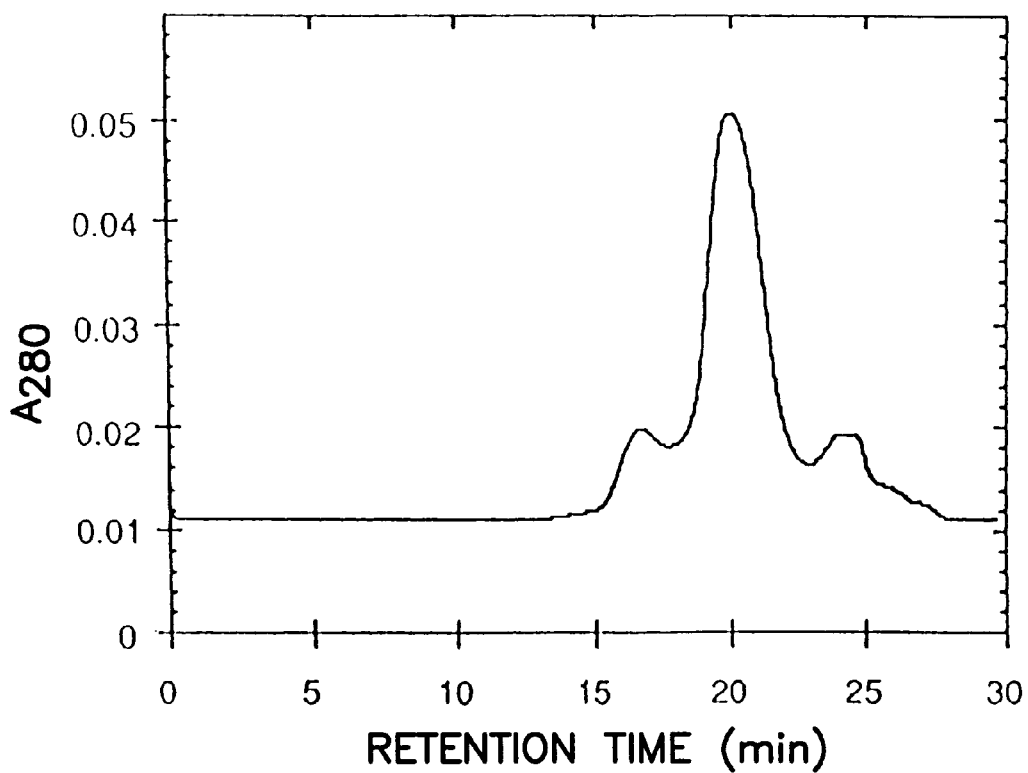
FIG. 4(C) depicts the hK2-containing fractions from the 22 minute peak from (B) were concentrated and applied to a Pharmacia S12 size exclusion column. Fractions were collected and analyzed by SDS/PAGE. The 19.4 minute peak appeared homogeneous by SDS-PAGE.

To purify hK2 polypeptides, the serum-free spent medium from AV12-pGThK2$^{v217}$ clone #2 was collected after 7 days, concentrated and subjected to anion exchange chromatography (FIG. 4A). The peak of hK2 activity eluted at approximately 0.2 M NaCl as determined by ELISA assays (dotted line). The ELISA assay correlated well with the appearance of a ~34 kD band of protein seen by SDS/PAGE in the same fractions. The hK2-positive fractions from the anion exchange column were collected and subjected to hydrophobic interaction chromatography (HIC) (FIG. 4B). A major portion of the A$_{280}$ was not retained on HIC column. The main peak retained on HIC, which eluted at 22 minutes, also showed the highest peak of activity by ELISA assay (dotted line, FIG. 4C). A major protein band at ~34 kD was also observed by SDS-PAGE. When the 22 minute peak from HIC was resolved by SEC, typically about 80–90% of the protein A$_{280}$ eluted at 19.4 minutes, a retention time consistent with a protein of approximately 34 kD (FIG. 4C). The only other protein peak on SEC, eluting at 16.7 minutes, corresponded to a ~70 kD protein observed in previous purification steps.

To further identify the purified protein, approximately 2.5 µg of the protein was subjected to automated N-terminal analysis which yielded the following sequence: Val-Pro-Leu-Ile-Gln-Ser-Arg-Ile-Val-Gly-Gly-Trp-Glu-(resdues 1–13 of SEQ ID NO:16). No competing sequence was evident from the profile of amino acids released sequentially by the Edman degradation procedure. By analogy to PSA this protein is phK2$^{v217}$, since the known sequence of mature PSA (isolated from seminal fluid) begins with Ileu-Val-Gly- and pPSA and phK2 have been postulated to have an extra 7 amino acids at the N-terminus (FIG. 2). Amino acid analysis of this protein yielded an amino acid composition consistent with the predicted sequence of phK2$^{v217}$. This phK2 polypeptide was purified in mg quantities.

EXAMPLE 3

Characterization of phK2$^{v217}$ and Generation of hK2$^{v217}$

Figure 5:
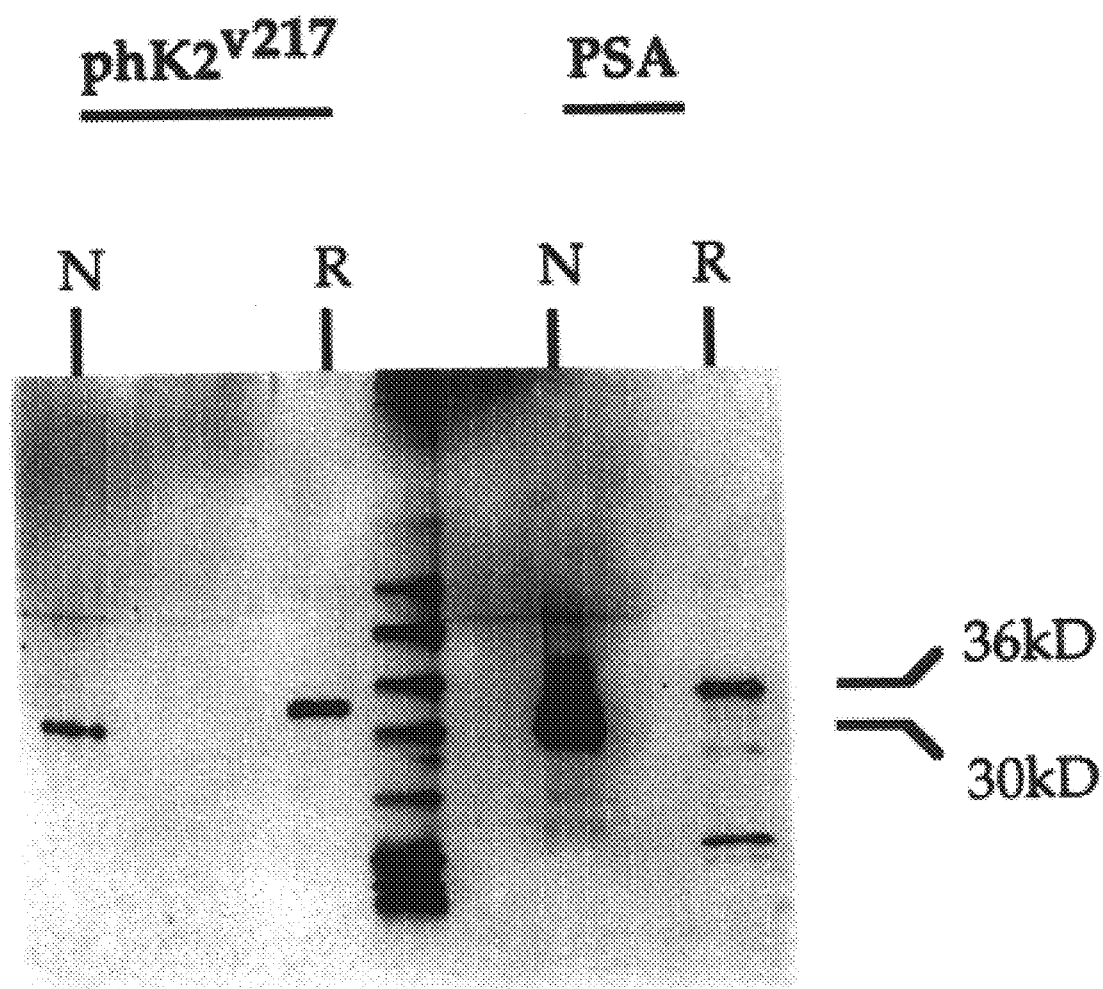
FIG. 5 represents an SDS/PAGE analysis of purified hK2 and PSA. A 1.5 mg sample of purified phK2$^{v217}$ or PSA was boiled in sample buffer with (R) or without (N) 1% beta-mercaptoethanol. Samples were subjected to SDS/PAGE on a 4–20% gel. The protein bands were visualized by staining the gel with silver.

To examine the efficiency of the purification scheme employed in Example 2, 1.5 µg of purified phK2$^{v217}$ was subjected to SDS/PAGE in the presence or absence of beta-mercaptoethanol (BME), and the gel was stained with silver. Results showed that the phK2$^{v217}$ in the sample was about 95% pure (FIG. 5). It also showed that phK2$^{v217}$ migrated at ~30 kD in the absence of BME, and at ~34 kD in the presence of BME. This pattern is similar to that observed for the PSA purified from seminal fluid (FIG. 5).

The amino acid sequence of hK2, deduced from the cDNA sequence, shows the presence of one potential N-linked glycosylation site at residue 78 (N-M-S). To determine if this site is glycosylated, phK2$^{v217}$ was subjected to SDS/PAGE, transferred to nitrocellulose paper, reacted with digoxigenin (DIG)-coupled lectins followed by horseradish peroxidase labeled anti-DIG.

Figure 6:
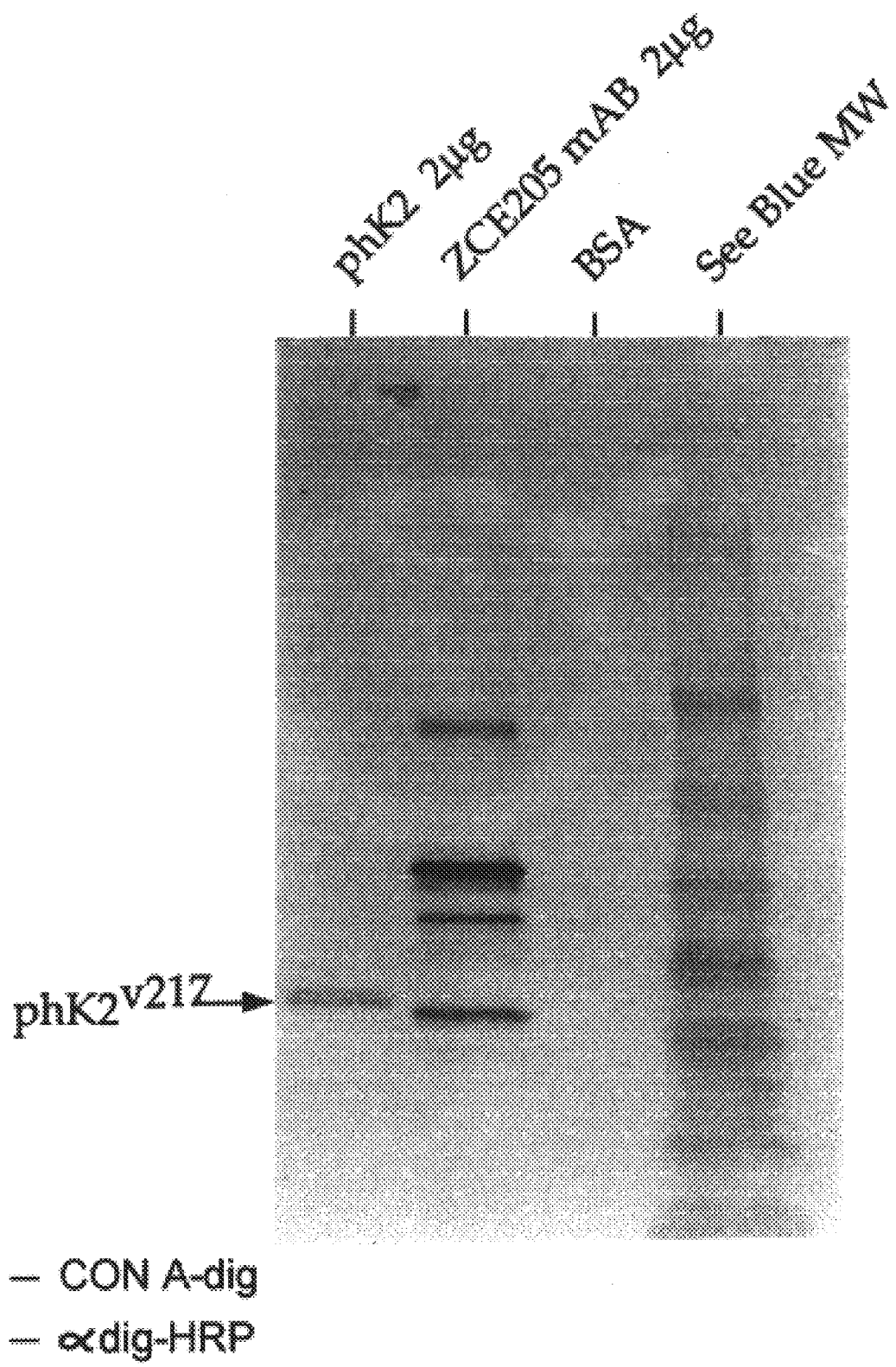
FIG. 6 depicts Conconavalin A staining of phK2$^{v217}$. The predicted position of phK2 is designated by an arrow. ZCE (an anti-CEA mAb) and BSA were included as examples of glycosylated and non-glycosylated proteins, respectively. The presence of a band at the predicted position in the phK2 lane demonstrates that this protein is glycosylated.

In FIG. 6 (lane 1), 2 µg of phK2 was stained with concanavalin A (Con A) suggesting the presence of two nonsubstituted or 2-O-substituted α-mannosyl residues in the protein. Lane 2 shows Con A staining of the positive control glycoprotein, ZCE025 mAB. Both the heavy chains (50 kD) and light chains (25 kD) of this mAb are known to contain N-linked oligosaccharides with mannose cores. Lane 3 shows that a nonglycosylated protein (BSA) fails to react with the Con A lectin. phK2$^{v217}$ also reacted with RCA (Gal b1-4GlcNAc specificity) and AAA, (α(1–6) linked fucose specificity). This pattern of lectin reactivity is consistent with the presence of complex N-linked oligosacharides. The oligosacharides on phK2$^{v217}$ also contains sialic acid since both SNA (sialic acid linked α(2–6) to galactose) and MAA (sialic acid linked α(2–6) to galactose were reactive with phK2$^{v217}$.

Figure 7:
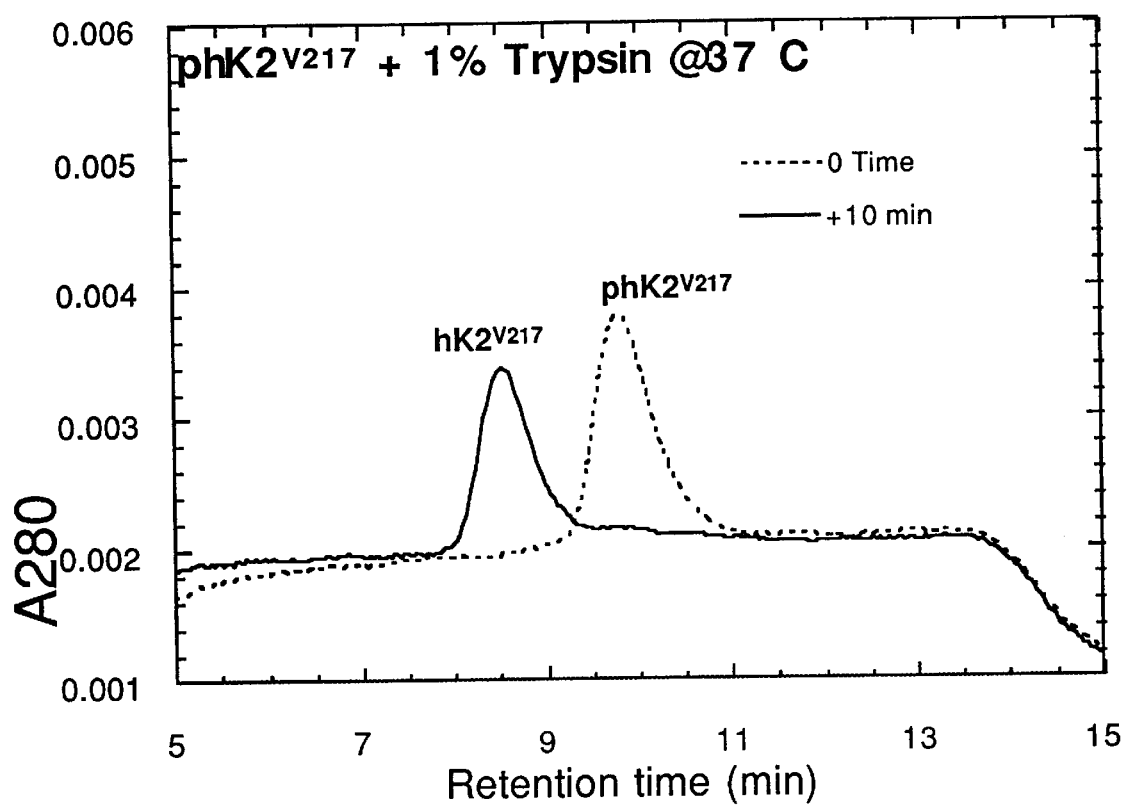
FIG. 7 represents the conversion of pro to mature hK2$^{v217}$ by trypsin cleavage. Trypsin (1% w/w) was incubated with phK2$^{v217}$ for 10 minutes at 37° C. in 100 mM borate buffer pH 8, and then subjected to HIC-HPLC. The dashed line represents the profile of the phK2$^{v217}$ prior to incubation with trypsin. The solid line represents the profile of phK2 after trypsin digestion. The profiles have been superimposed for comparison. The identity of the two forms was confirmed by N-terminal sequencing of the protein.

The sequence of the pro region of hK2 is VPLIQSR (residuse 1–7 of SEQ ID NO:16). An enzymatic cleavage at the carboxy-terminal end of the arginine in this pro sequence would convert phK2 to hK2. A mild trypsin digestion was developed to hydrolyze the peptide bond of purified phK2$^{v217}$ at this position. phK2$^{v217}$ was incubated with 1% trypsin and the conversion was monitored by HIC-HPLC (FIG. 7). This procedure resulted in a complete conversion of phK2$^{v217}$ to hK2$^{v217}$. The peak designated hK2$^{v217}$ was N-terminally sequenced and shown to begin with the sequence, IVGGWE, which is the N-terminus for the mature form of hK2. No sequence other than the above was detected demonstrating that this mild trypsin treatment does not result in any significant level of non-specific cleavage. SDS/PAGE of trypsin-treated samples showed a small but discernible increase in mobility, generally consistent with a minor reduction in mass of 826 daltons, the mass of the pro peptide.

EXAMPLE 4

Generation of hK2-Specific Abs phK2$^{v217}$ and hK2$^{v217}$ were used as immunogens to generate mAbs against hK2. Hybridomas were screened based on high reactivity with hK2$^{v217}$ or phK2$^{v217}$ and minimal reactivity with PSA. Representatives of mAbs obtained from the hybridomas are shown in Table 1. Immunization with phK2$^{v217}$ resulted in mAb HK1G586.1 and HK1G 464.3. HK1G586.1 was hK2-specific, since it recognized both phK2$^{v217}$ and hK2$^{v217}$ but not PSA. On the other hand, HK1G464 was phK2-specific, since it only recognized phK2$^{v217}$ and not hK2$^{v217}$ or PSA.

TABLE 1

Specificity of various mAbs raised to hK2$^{v217}$ and phK2$^{v217}$

A. mAbs raised to phK2$^{v217}$

| mAbs | PSA | hK2$^{v217}$ | phK2$^{v217}$ |
|---|---|---|---|
| Irrelevant Ab | 0.245 | 0.162 | 0.125 |
| positive control | 2.242 ± 0.06 | 9.196 | 8.91 ± 0.02 |
| HK1G586.1 (10 µg/ml) | 0.150 ± 0.004 | 11.154 ± 0.18 | 10.146 ± 0.87 |
| HK1G464.3 (Ascites 1:2000) | 0.143 ± 0.03 | 0.245 ± 0.02 | 6.644 ± 0.17 |

B. mAb raised to hK2$^{v217}$

| mAb tested | PSA | hK2$^{v217}$ | phK2$^{v217}$ |
|---|---|---|---|
| Irrelevant Ab | 0.157 ± 0.18 | 0.132 ± 0.01 | 0.153 ± 0.01 |
| Positive control | 2.768 ± 0.08 | 8.342 ± 1.3 | 9.673 ± 0.99 |
| Media only (neg. control) | 0.129 ± 0.02 | 0.240 ± 0.02 | 0.247 ± 0.01 |
| HK1H247 | 0.157 ± 0.01 | 9.34 ± 0.7 | 0.179 ± 0.004 |

Immunization with hK2$^{v217}$ resulted in mAb HK1H247. This mAb was hK2-specific since it recognized only hK2$^{v217}$ but not phK2$^{v217}$ or PSA. These results show that phK2$^{v217}$ and hK2$^{v217}$ are invaluable as immunogens in generating mAbs specific for different forms of hK2.

Western blot analysis was used to examine if HK1G586 recognizes hK2 in seminal fluid (FIG. 8). hK2-immunoreactive bands at ~22 kD, ~33 kD, and ~85 kD were recognized by this mAb. A similar hK2-immunoreactive pattern in seminal fluid was also recently reported by Deperthes et al., Biochem. Biophy. Acta, 1245, 311 (1995). This result indicates that a mAb raised to hK2$^{v217}$ recognizes native hK2 in seminal fluid. All the antibodies raised to hK2$^{v217}$ or phK2$^{v217}$ also recognized the corresponding form of hK2 and phK2 indicating that hK2 and phK2 are immunologically similar to hK2$^{v217}$ and phK2$^{v217}$, respectively (see below).

EXAMPLE 5

Expression of hK2 in Mammalian Cells

To express wild type hK2 (hK2) in mammalian cells pGThk2 (FIG. 3) was transfected into AV12 cells. Several clones expressing an hK2 polypeptide were identified by Western analysis using HK1D 106.4 (a hK2-specific mAb raised to a polypeptide corresponding to amino acid residues 17–71 of hK2). Clone AV12-hK2#27 (AV12-hK2) was selected for further analysis based on its higher hK2 expression level. Cells transfected with vector alone (pGTD) showed no reactivity with HK1D 106.4.

ELISA using HK1D 106.4 mAb indicated the presence of ~0.5–1 µg/ml of an hK2 polypeptide in the serum-free spent medium of AV12-hK2 at day 7. The same method used in purification of phK2$^{v217}$ from AV12-hK2$^{v217}$ was used to purify hK2 polypeptides from the day 7 spent medium of AV12-hK2. This resulted in low yields of purified hK2 polypeptides which were highly unstable to the purification procedures and thus impractical to be used as immunogen.

hK2 polypeptides were partially purified using the above method, subjected to SDS/PAGE, electroblotted and subjected to N-terminal amino acid sequencing. This analysis indicated that the hK2 polypeptide in the spent medium of AV12-hK2 at day 7 has the sequence, IVGGWECEK at N-terminus. No competing sequence was evident from the profile of amino acids released sequentially by the Edman degradation procedure. By comparison to PSA, this sequence corresponds to mature hK2 (hK2). Amino acid analysis of this protein was also consistent with that of hK2.

This finding was intriguing since it showed that predominantly phK2$^{v217}$ was present in the serum-free spent medium of AV12-hK2$^{v217}$ at day 7, whereas predominantly hK2 was present in the serum-free spent medium of AV12-hK2 at day 7. To examine the form of hK2 present in the serum-free medium of AV12-hK2 at day 1 this material was partially purified by affinity purification using HK1G 586.1 mAbs. The ~34 kD protein was transferred onto PVDF and was subjected to N-terminal analysis revealing a sequence, VPLIQSRIVGG (residuse 1–16 of SEQ ID NO:16). No competing sequence was evident from the profile of amino acids released sequentially by the Edman degradation procedure. Compared with PSA, this sequence corresponds to phK2. This suggests that the hK2 polypeptide is secreted as the pro form by both AV12-hK2 and AV12-hK2$^{v217}$ cells. However, while phK2$^{v217}$ is stable and is not converted to hK2$^{v217}$, phK2 is unstable and is easily converted to hK2 extracellularly.

EXAMPLE 6

Biosynthesis of hK2

Figure 9:
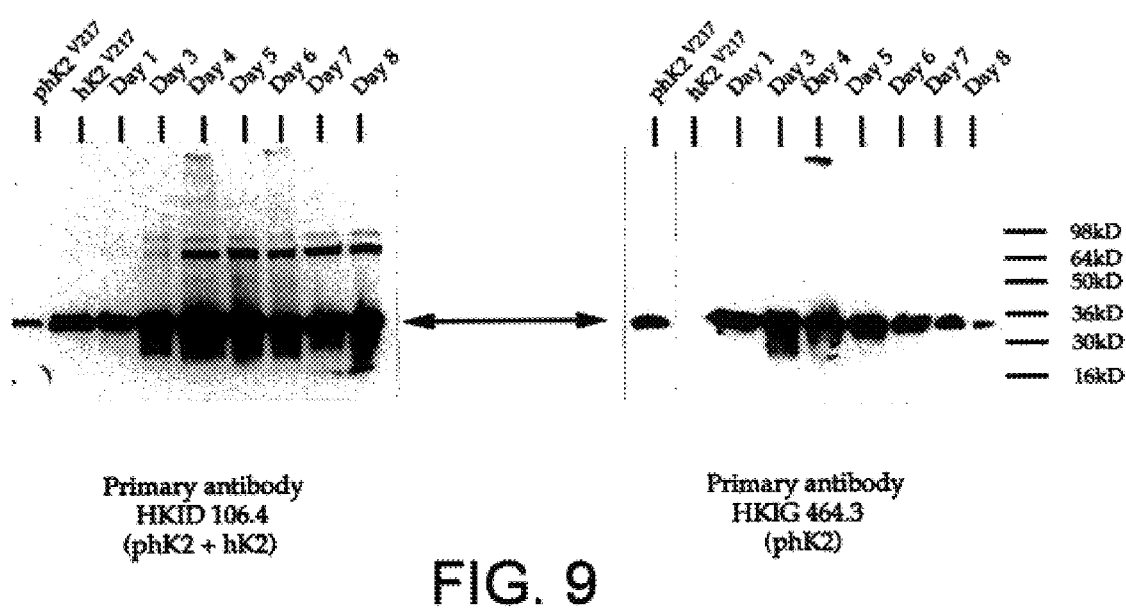
FIG. 9 represents a time course study of hK2 expression in cells from AV12-hK2 clone #27 was grown to ~60–70% confluency, then cells were washed with HBSS and serum free HH4 media was added. Spent medium was withdrawn each day, concentrated and subjected to SDS/PAGE on a 12% gel. Proteins were electroblotted and probed with monoclonal antibody HK1D 106.4, which detects both phK2 and hK2 (1:1000). The blot was developed with ECL (Amersham) according to the manufacturer's instructions. Purified phK2$^{v217}$ and hK2$^{v217}$ were used as controls. The position of hK2 is indicated by the arrow.

To further study the biosynthesis of hK2 in mammalian cells, a time course study was conducted where serum-free spent media from AV 1 2-hK2 clone #27 was collected each day for 8 consecutive days, concentrated and subjected to SDS/PAGE. The proteins were transferred to nitrocellulose membrane and probed with either HK1D 106.4 or HK1G 464.3 mAbs (FIG. 9). As also shown in FIG. 9, HK1D 106.4 recognizes both phK2 and hK2 whereas HK1G 464.3 recognizes only phK2 as its epitope lies in -7 to +7 region of hK2. Expression of hK2 polypeptides (~34 kD) peaked by day 3 and plateaued thereafter as detected by HK1D 106.4 mAbs. Two other immunoreactive bands migrating at ~70 kD and ~90 kD were also detected from day 4 onwards.

On the other hand, when the same samples were blotted and probed with HK1G 464.3, a gradual reduction in the level of hK2 was detected by day 4. By day 8, very low levels of hK2 were found in the spent medium. This result shows that phK2 is being secreted into the media by AV12-hK2 cells and is gradually converted to hK2 extracellularly. Curiously, ~70 kD and ~90 kD bands were not observed with HK1G 464.3 mAbs indicating that these bands are either homo-oligomers of hK2 or are hK2 covalently complexed with a yet unknown protein(s). Even though the identity of these bands is not known at this time, they serve as markers for the presence of hK2 in the spent media. In FIG. 9, purified phK2$^{v217}$ and hK2$^{v217}$ proteins were used as controls.

Figure 10:
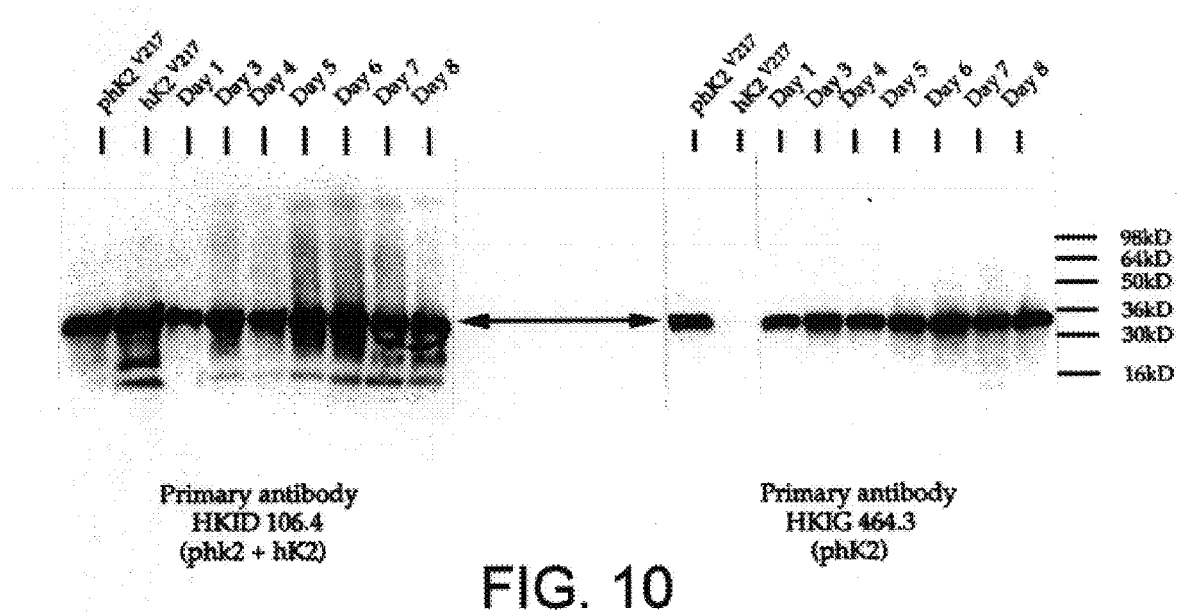
FIG. 10 represents a time course study of expression of the variant form of hK2 in transfected AV12 cells. At ~60–70% confluency, AV12-hK2$^{v217}$ cells were washed with HBSS and serum free HH4 media was added. Spent media was withdrawn each day, concentrated and subjected to SDS/PAGE on a 12% gel. Proteins were electroblotted and probed with a preparation of monoclonal antibody HK1D 106.4 Goat anti-mouse IgG-HRP (1:500) was used as a secondary antibody and the blot was developed with ECL (Amersham) according to the manufacturer's instructions. Purified phK2$^{v217}$ and hK2$^{v217}$ were used as controls. The position of hK2 is indicated by the arrow.

To study the biosynthesis of hK2$^{v217}$ in AV12 cells a similar time course study was conducted on AV12-hK2$^{v217}$ clone #2. As shown in FIG. 10, expression of hK2$^{v217}$ polypeptides peaked by day 3 and did not vary much from day 4 onwards as detected by HK1D 106.4 mAbs. Similar results were obtained when the blot was probed with HK1G 464.3 mAbs (FIG. 10). This indicated that AV12-pGThK2$^{v217}$ clone #2 cells are expressing phK2$^{v217}$ from day 1 onwards and that for at least 8 days thereafter, this protein is not converted to the mature form. These results are in contrast with those of phK2, which is converted to hK2 if left in the media for 8 days, indicating that phK2$^{v217}$ is stable in media at 37° C. for 8 days.

Figure 11:
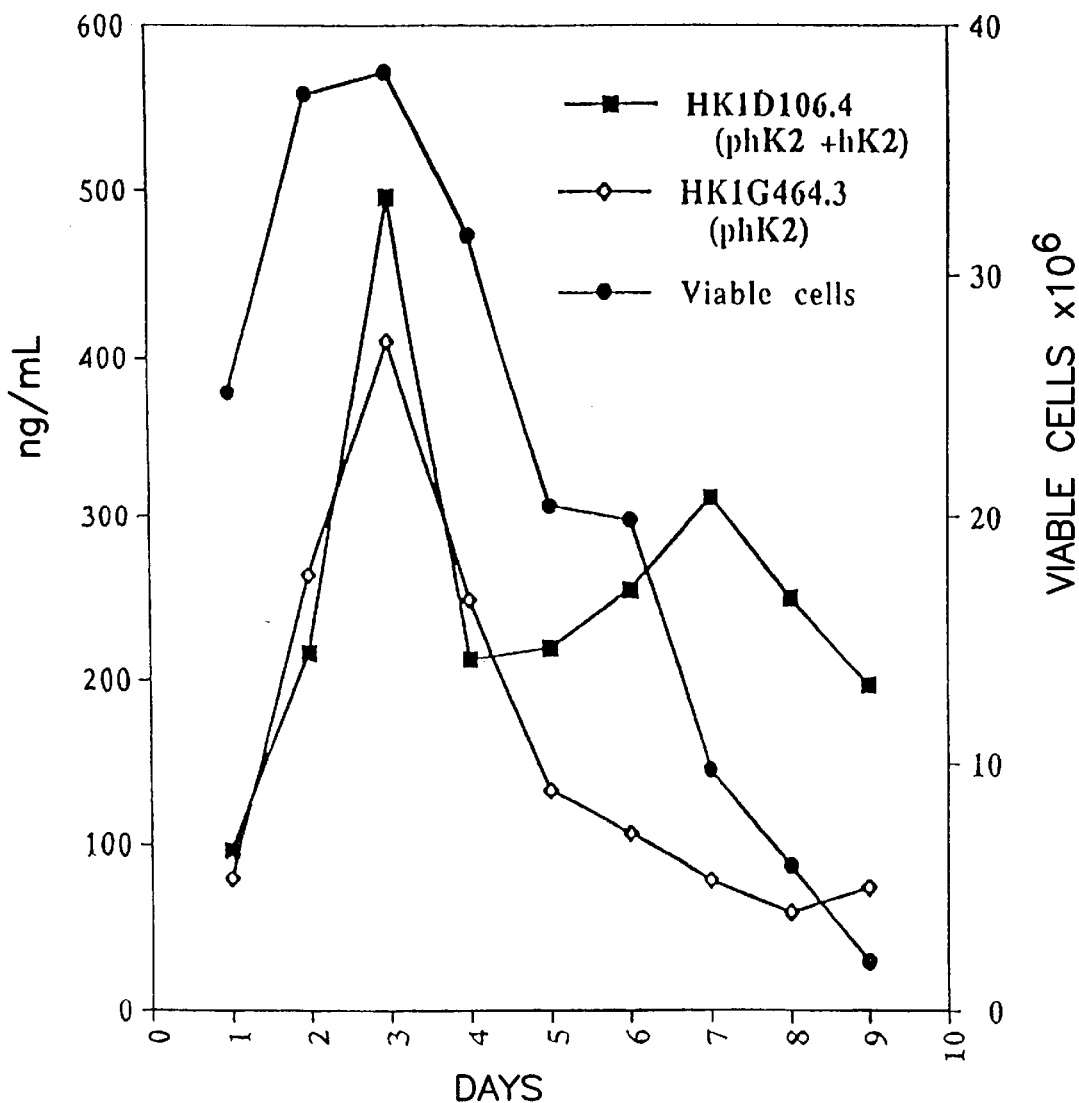
FIG. 11 is a plot of hK2 expression and cell viability over time. AV12-hK2 clone #27 was grown to 60–70% confluency, washed with HBSS and serum free HH4 media was added. Spent media was withdrawn each day and the hK2 concentration was measured by ELISA using HK1D 106.4 or HK1G 464.3 as a primary antibody, and goat anti-mouse IgG-HRP as a secondary antibody. The reaction was developed with OPD (Sigma, St. Louis, Mo.). Viable cells were enumerated daily using trypan blue dye exclusion.

To study whether extracellular conversion of phK2 to hK2 correlates with the viability of AV12-hK2 clone #27 cells in culture, clone #27 cells were counted using trypan blue exclusion. Expression of hK2 in the spent medium was measured by ELISA using both HK1D 106.4 and HK1G 464.3 mAbs. As shown in FIG. 11, the number of viable cells peaked at 38 million in culture by day 3 and gradually decreased thereafter. By day 8, the number of viable cells were reduced to less than 10 million. The expression of phK2 (measured by HK1G 464.3) also peaked by day 3 and gradually declined thereafter.

On the other hand, expression of hK2 (measured by HK1D 106.4) peaked by day 3 but plateaued thereafter. This result indicates that phK2 is secreted by AV12-hK2 cells and a fraction of it is gradually converted extracellularly to hK2 by day 4. Moreover, it shows that conversion of phK2 to hK2 clearly correlates with a decrease in cell viability, indicating that the extracellular proteases released by the dying cells may be one of the factor(s) responsible for this conversion. Expression of hK2 was highest at the point in which cells were most viable. A decrease in hK2 paralleled a decrease in cell viability, suggesting the hK2 is secreted by these cells, as opposed to being released following cell death and lysis. Also, a rise in hK2 corresponded to a drop in phK2, indicating that the pro form of hK2 was automatically converted to the mature form over time.

To examine the biosynthesis of hK2 in prostate carcinoma cells hK2 was expressed in DU145 and PC3 cell lines. pphK2 was cloned into plasmids pLNCX and pLNSX (Miller and Rosman, BioTechniques, 7, 980 (1989)), under the control of the CMV and SV40 promoters, respectively. The resulting plasmids, pLNC-hK2 and pLNS-hK2, respectively, were transfected into PC3 and DU145 cells, respectively, and clones were selected in media containing G418. Clones expressing high levels of hK2 were selected (PC3-hK2 and DU145-hK2) by ELISA and Western blots.

Figure 12:
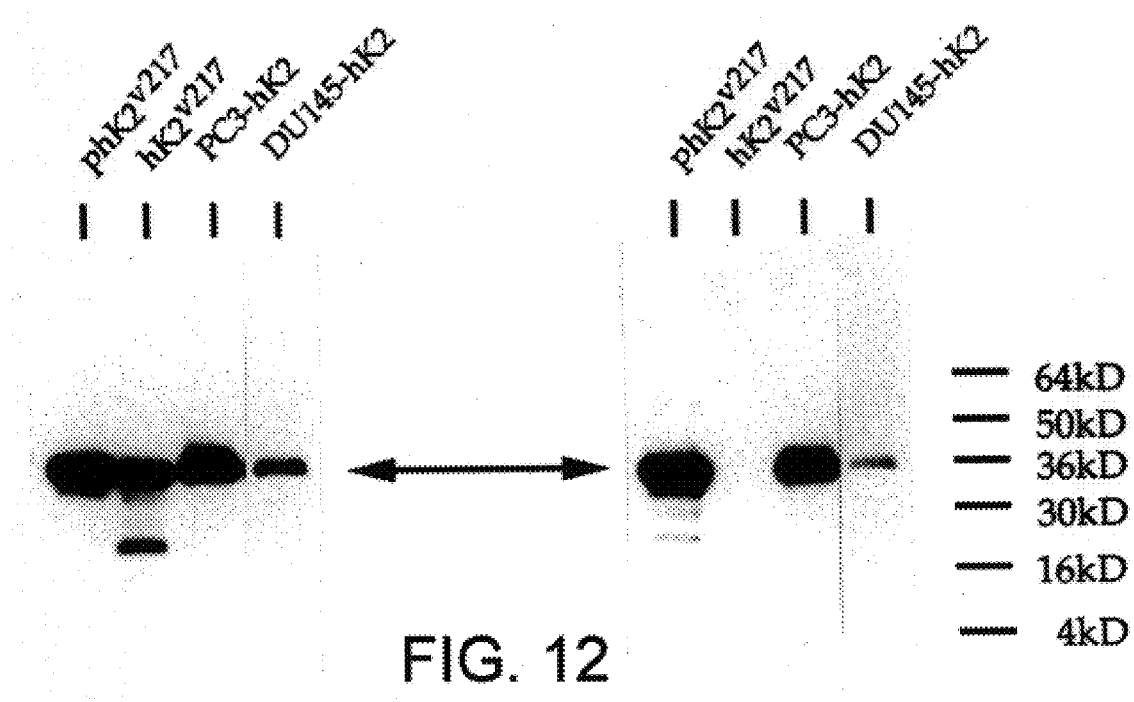
FIG. 12 depicts the expression of hK2 in PC3 and DU145 cells. PC3 and DU145 cells transfected with pGThK2 were grown to ~60–70% confluency, washed and resuspended in serum free HH4 media. The spent medium of pGThK2 transfected DU145 cells was collected 3 days after resuspension and the spent medium of pGThK2 transfected PC3 cells was collected 5 days after resuspension. Spent media were concentrated and subjected to SDS/PAGE on 12% gels. Proteins were electroblotted and probed with HK1D 106.4. Purified phKv2$^{v217}$ and phK2$^{v217}$ were used as controls. The position of hK2 is indicated by an arrow.

To assess the level of hK2 and phK2 in the media, serum-free medium of PC3-hK2 and DU145-hK2 cells were subjected to Western blot analysis using HK1D 106.4 (hK2-specific) and HK1G 464.3 (phK2-specific) mAbs (FIG. 12). Results showed that phK2 is present in the spent medium of both DU145-hK2 and PC3-hK2. This indicates that in prostate carcinoma cells hK2 is secreted as phK2 and is converted to the mature form extracellularly. This finding confirms the results previously obtained with AV12 cells. Predominantly phK2 was detected in the spent medium of PC3-hK2 cells even after 7 days, however, predominately hK2 was present in the serum-free medium of DU145-hK2 starting from day 1. This is probably due to abundance of extracellular proteases in DU145 spent medium.

Figure 13:
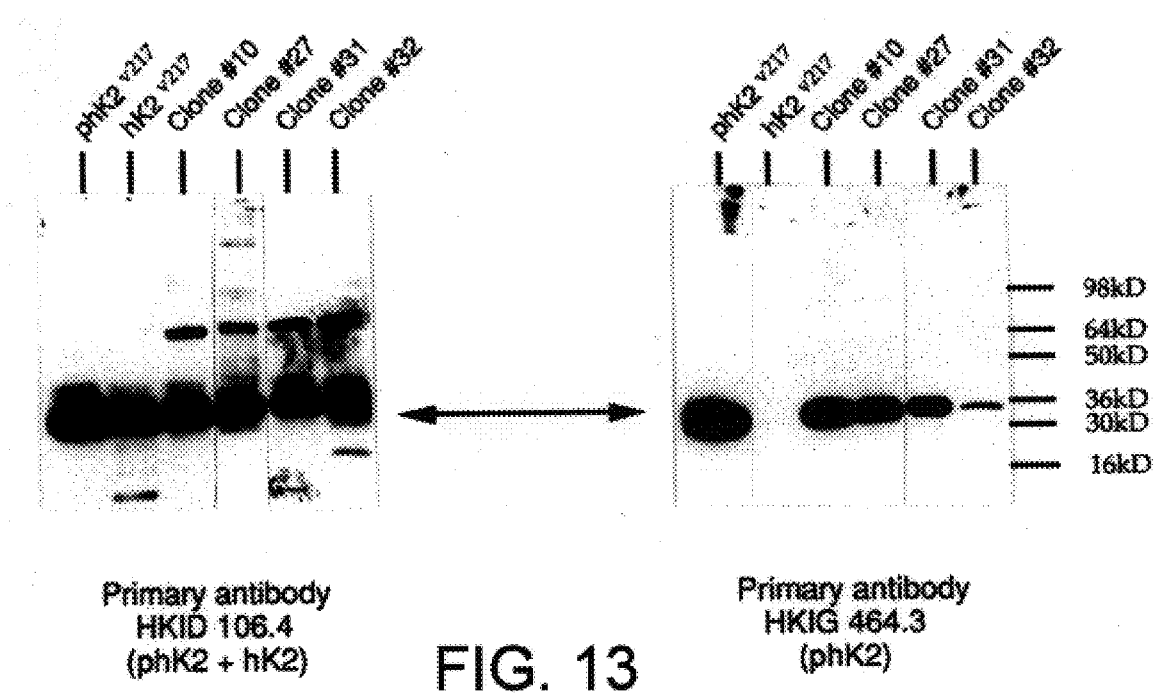
FIG. 13 depicts the expression of hK2 by selected hK2-containing AV12 clones. Cells from hK2 containing AV12 clone numbers 10, 27, 31 and 32 were grown to ~60–70% confluency and washed with HBSS, then serum free HH4 media was added. Spent media was withdrawn 7 days after the addition of serum free media, concentrated and subjected to SDS/PAGE on a 12% gel. Proteins were electroblotted and probed with HK1D 106.4. Goat anti-mouse IgG-HRP (1:500) was used as a secondary antibody and the blot was developed with ECL (Amersham) according to the manufacturer's instructions. Purified ph2$^{v217}$ and hK2$^{v217}$ were used as controls. The position of hK2 is indicated by an arrow.
Figure 14:
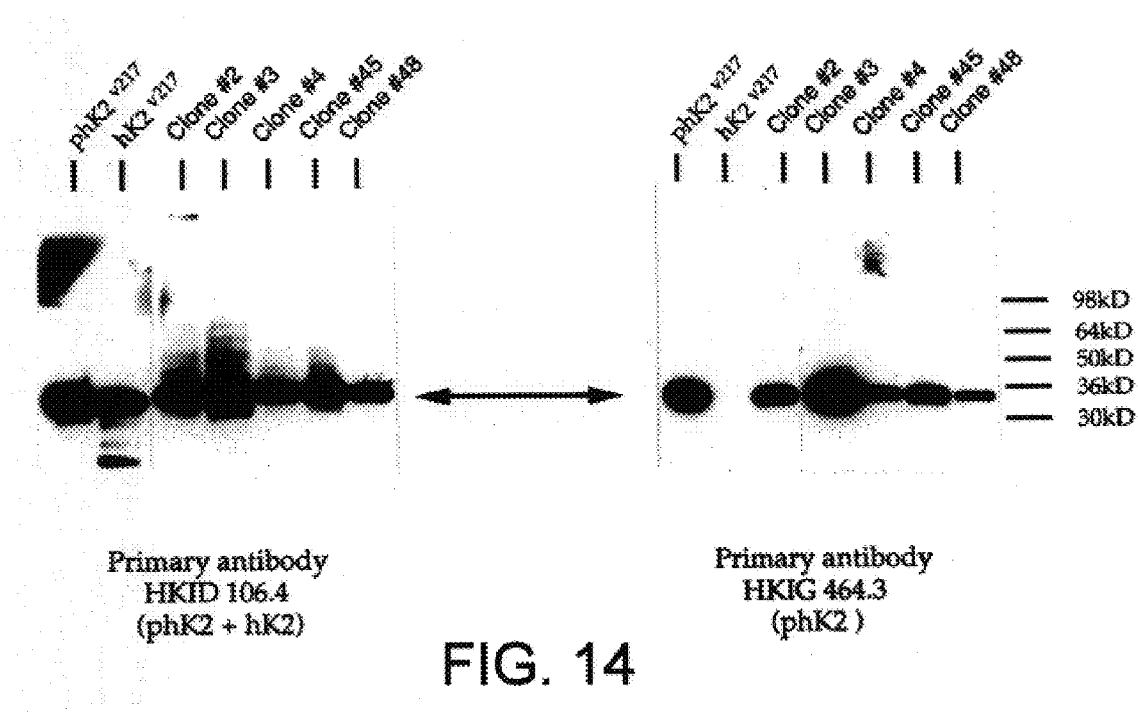
FIG. 14 depicts the expression of phK2$^{v217}$ in selected AV12-hK22$^{v217}$ clones. Cells from AV12 clone numbers 2, 3, 4, 45 and 48 were grown to approximately 60–70% confluency and washed with HBSS, and serum free HH4 media was added. Spent media was withdrawn 7 days after the addition of serum free media, concentrated and subjected to SDS/PAGE on a 12% gel. Proteins were electroblotted and probed with HK1D 106.4. Goat anti-mouse IgG-HRP (1:500) was used as secondary antibody and the blot was developed with ECL (Amersham) according to the manufacturer's instructions. Purified phK2$^{v217}$ and hK2$^{v217}$ were used as controls. The position of hK2 is indicated by an arrow.

To examine whether the above results were limited to just one clone, 3 other independently isolated clones of AV12-hK2 and 4 other independently isolated clones of AVl2-hK2$^{v217}$ were tested for the expression of hK2 polypeptides. Serum-free spent medium of the clones were collected at day 7 and tested for the expression of hK2 by Western blots using HK1D 106.4 (hK2-specific) and HK1G 464 (phK2-specific) mAbs (FIGS. 13 and 14). In all of the AV12-hK2 clones, HK1D 106.4 mAb detected not only the major ~34 KD band ("hK2") but also the ~70 kD and the ~90 kD bands that are indicative of the presence of hK2 (FIG. 13). HK1G 464.3 detected very low levels of phK2 in all of the AV12-hK2 clones (FIG. 14). This result indicates that predominantly hK2 is present in the spent medium of all the AV12-hK2 clones verifying the biosynthetic mechanism established for AV12-hK2 #27 clone. The same analyses were used on AV12-hK2$^{v217}$ clones (FIG. 14). Results indicated that only phK2$^{v217}$ was present in the spent medium of these clones at day 7 verifying our findings with the AV 2Ihk2$^{v217}$ clone.

The above results collectively suggest that hK2 is expressed as the pro form in mammalian cells and is converted to mature form extracellularly by as yet unknown proteases. These results also suggest that phK2 may be present in the biological fluids and therefore can be a useful diagnostic marker for pCa and BPH.

EXAMPLE 7

Enzymatic Activity and Specificity of hK2 and hK2$^{v217}$

A small amount of hK2 was purified to sufficient purity to establish its enzymatic activity and substrate specificity. The general activity of hK2 was measured by determining its amidolytic activity chromogenically on p-nitroanilide derivatives of peptides (Table 2). The p-nitroanilide released by proteolytic digestion of these substrates is measured at absorbance $A_{405}$. The substrate methoxysuccinyl-Arg-Pro-Tyr-para-nitroanilide (MeO-Suc-R-P-Y-pNA) is used to measure chymotrypsin-like proteases which cleave at the phenylalanine. This substrate has been used previously to measure the activity of PSA (Christensson et al., Eur. J. Biochem., 194, 755 (1990)). The substrate H-D-Pro-Phe-Arg-para-nitroanalide (P-F-R-pNA) is specific for trypsin-like proteases which cleave at arginine (R).

hK2 was found to have overall activity more than 10 times higher than hK2$^{v217}$ on P-F-R-pNA and neither protein showed an ability to hydrolyze MeO-Suc-R-P-Y-pNA, the chymotrypsin substrate. Other comparable substrates containing trypsin-like sites for cleavage (lysine, arginine) were also tested and hK2 was found to hydrolyze the substrate P-F-R-pNA with the highest rate. These findings indicate that hK2 has trypsin-like activity.

TABLE 2

| | Amidolytic Activity on Chromogenic Substrates | |
| --- | --- | --- |
| Protease | MeO-Suc-R-P-Y-pNA xmol/min/µg/ml | P-F-R-pNA xmol/min/µg/ml |
| hK2$^{v217}$ | 0 | 8.7 pmol |
| hK2 | 0 | 4.1 nmol |
| PSA | 13.3 pmol | 2.2 pmol |
| Trypsin | 3.8 pmol | 25.5 nmol |

Table 2: Amidolytic activity of hK2, hK2$^{v217}$, PSA and trypsin on chromogenic substrates.

Figure 15:
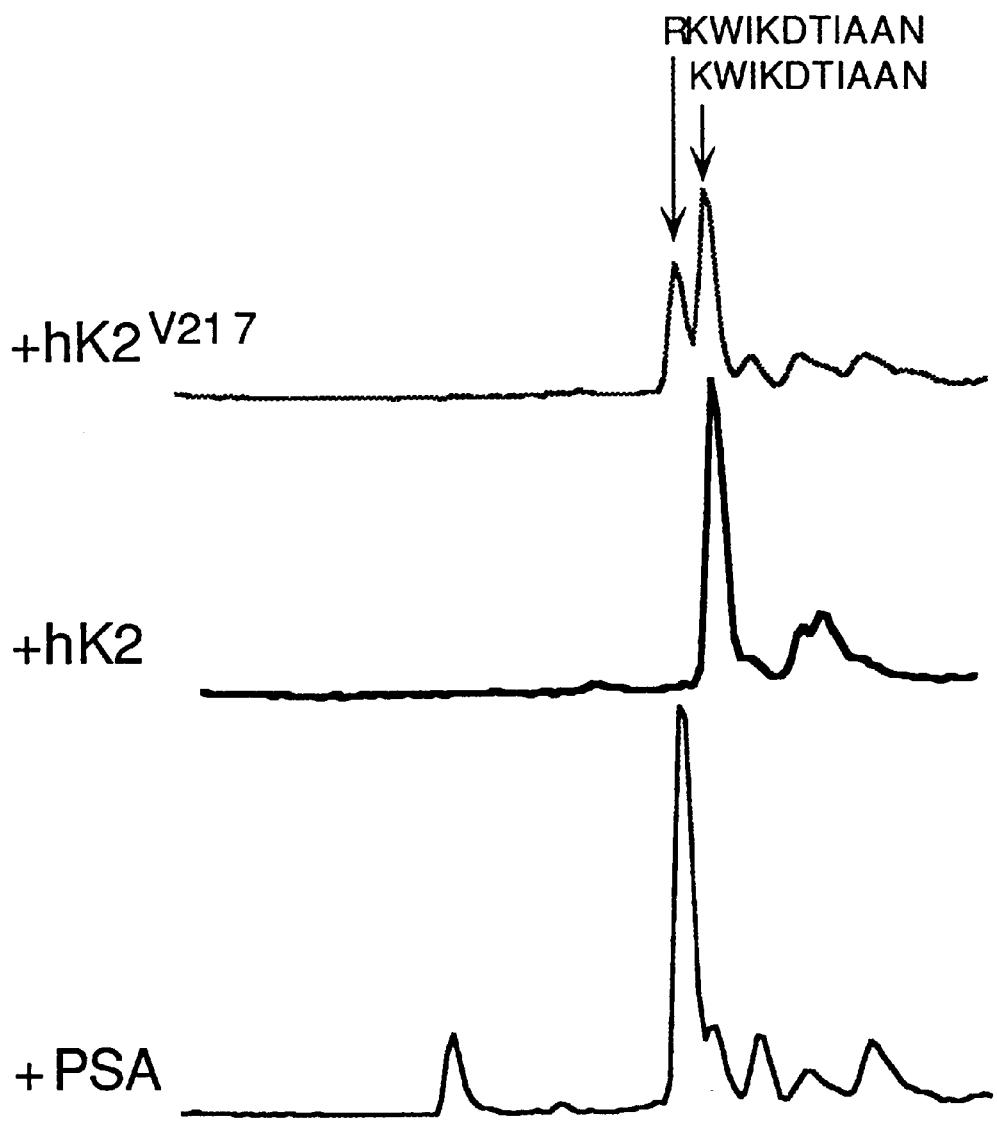
FIG. 15 depicts the amidolytic specificity of hK2$^{v217}$, hK2, and PSA for residues 210–236 of hK2 SEQ ID NO:18. The synthetic peptide (0. 63 mM) was digested overnight at 37° C. with 1 µg/ml hK2, 40 µg/ml hK2$^{v217}$ or 100 µg/ml PSA, and the digestion products separated by RP-HPLC. Peaks were normalized to compare the qualitative aspects of cleavage.

The specificity of hK2 and hK2$^{v217}$ was examined in more detail by the use of peptide substrates together with N-terminal amino acid sequence analysis to determine which peptide bonds had been hydrolyzed. FIG. 15 shows amidolytic activity on the polypeptide CALPEKPAVYTKVVHYRKWIKDTIAAN(SEQ ID NO:18), which has both potential trypsin and chymotrypsin cleavage sites. hK2$^{v217}$ cleaved at both a trypsin (R-K) and chymotrypsin (Y-R) site with the trypsin-like cleavage at a 2:1 ratio over the chymotrypsin-like cleavage. As a control in these experiments phK2$^{v217}$ was also incubated with this peptide and showed no amidolytic activity. hK2 showed specificity different than hK2$^{v217}$ towards this peptide substrate. No chymotrypsin-like specificity was seen for hK2 on this substrate and its activity was exclusive for the trypsin-like site (R-K). None of the other lysine (K) residues in this polypeptide were hydrolyzed indicating that the specificity of hK2 was exclusive for the arginine (R) residue.

As a control trypsin was also studied on this substrate and cleaved all lysine (K) and arginine (R) sites except the K-P bond which is known not to be a site suitable for trypsin cleavage. Trypsin cleaved the R-K site of the 210–236 substrate (peptide #1, FIG. 16) at rates approximately 4X faster than hK2 and ~4000X faster than hK2$^{v217}$. No chymotrypsin-like bonds were cleaved by trypsin. PSA cleaved the Y-R bond primarily. A minor trypsin-like activity on the R-K bond was also seen for PSA (FIG. 15). This was consistent with the minor trypsin-like activity previously seen for PSA on the chromogenic substrate (Table 2).

Several other peptide substrates were also incubated with hK2 and PSA (FIG. 16). In all of the peptides tested, hK2 had specificity only for selected arginines, and PSA primarily for selected tyrosine (Y), phenylalanine (F) and leucine (L) residues. Only peptide #1 in FIG. 16 was cleaved by hK2$^{v217}$ as detailed by the chromatograms in FIG. 15.

EXAMPLE 8

Activation of phK2$^{v217}$ by hK2

The sequence of peptide #3 in FIG. 16 corresponds to amino acid residue −7 to +7 of phK2. This region contains the pro peptide, VPLIQSR(residuse 1–7 of SEQ ID NO:16), which is found as an N-terminal leader peptide in phK2$^{v217}$. As mentioned above, hK2 was able to cleave this peptide releasing the propeptide region, but hK2$^{v217}$ was not. To delineate if hK2 can cleave this pro sequence on a native substrate, its ability to convert phK2$^{v217}$ to hK2$^{v217}$ was monitored. phK2$^{v217}$ was incubated with 1% hK2 and the conversion was monitored by the HIC-HPLC method (FIG. 17A). Results showed that hK2 was able to convert phK2$^{v217}$ to hK2$^{v217}$, albeit at a rate ~30X slower than trypsin. When phK2$^{v217}$ was incubated with 40% hK2$^{v217}$, no difference in the ratios of the two hK2 forms was detected even after 6 hours (FIG. 17B). This corroborated previous observations with the peptide substrate and showed that, even on a native substrate, only hK2 and not hK2$^{v217}$ cleaved the pro region of hK2.

These results collectively demonstrate the stability of phK2$^{v217}$ and hK2$^{v217}$ upon extended incubation. When compared with hK2$^{v217}$, hK2 was shown to have a higher proteolytic activity, higher degree of specificity and, in particular, to have a specificity for the pro form of hK2 as demonstrated by activity on the pro peptide in FIG. 15 and its activity toward phK2$^{v217}$ in FIG. 17.

These results demonstrate a significant difference in enzymatic activity between hK2 and hK2$^{v217}$ and may help explain the low yields associated with attempts to purify hK2 from the medium compared to phK2$^{v217}$. Highly purified preparation of hK2 may not be stable due to autolysis as seen for other active proteases. These results further suggest that, in addition to immunological tests, enzymatic activity on hK2-specific substrates could be used to monitor the level of this protein in bodily fluids.

EXAMPLE 9

Formation of Inhibitor Complexes with hK2

Figure 18:
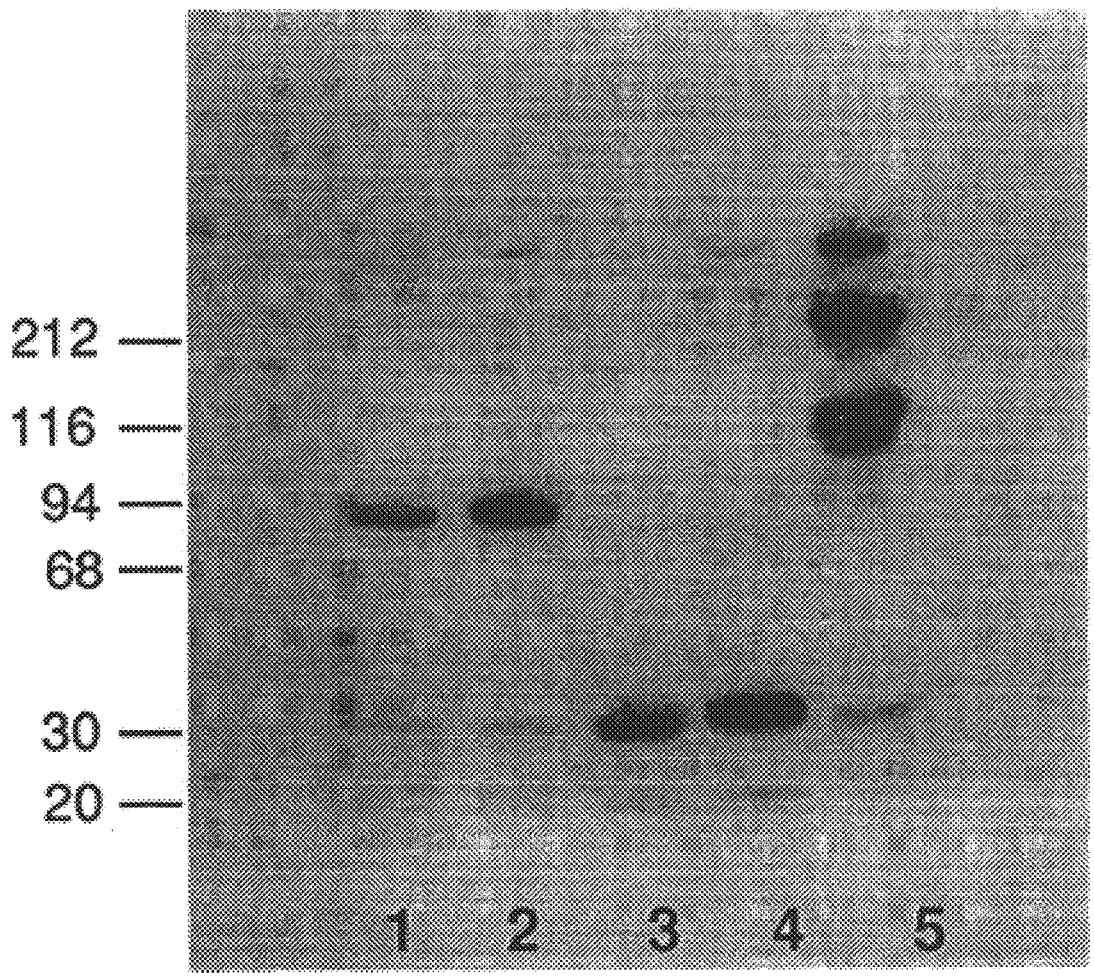
FIG. 18 depicts Western blot analysis of hK2 incubated with protease inhibitors. Each sample was separated on a 8–25% gradient SDS-PAGE, blotted and probed with HK1G586.1. hK2 was incubated for 4 hours at 37° C. with the following inhibitors: Lane 1, antichymotrypsin (ACT); lane 2, alpha 2-antiplasmin; lane 3, anti-thrombin III; lane 4, alpha 1-protease inhibitor (anti-trypsin); lane 5, alpha 2-macroglobulin; lanes 1 and 2 show a covalent complex of the predicted Mr of 90–100 kD. Serpin inhibitors were employed at 20 µM, macroglobulin at 2.8 µM, and hK2 at 0.175 µM. Lane 5 shows the higher Mr complexes representing covalent complex formation of hK2 with alpha 2-macroglobulin.
Figure 19:
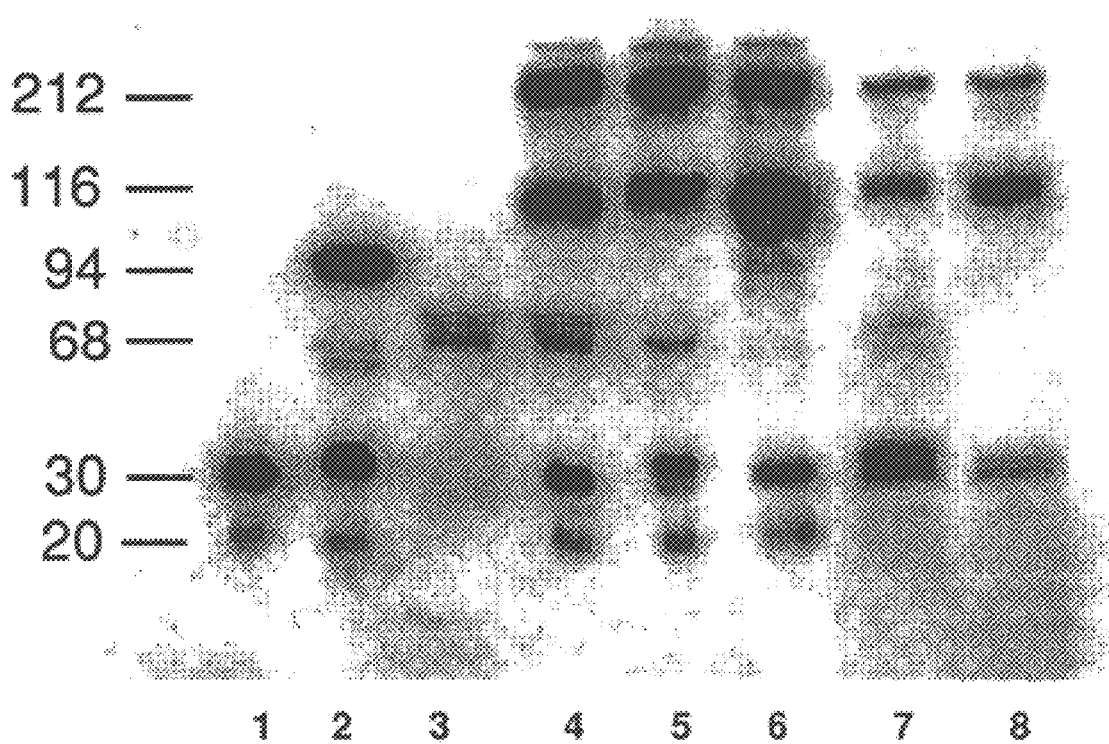
FIG. 19 depicts complex formation of hK2 in human serum. Western blots of hK2 and PSA were incubated with human serum. hK2 samples were probed with HKIG586.1 and PSA samples with PSM773 anti-PSA mAb. Lanes 1–6 contain hK2 samples and lanes 7 and 8 are PSA samples. Lane 1 represents an hK2 control. Lane 2 contains hK2 incubated with ACT for 4 hours. Lane 3 represents a serum control with no added protease. Lane 4 contains hK2 incubated for 15 minutes with serum. Lane 5 contains hK2 incubated with serum for 4 hours. Lane 6 contains hK2 incubated with purified alpha-2 macroglobulin for 4 hours. Lane 7 contains PSA incubated with serum for 4 hours. Lane 8 contains PSA incubated with purified alpha-2 macroglobulin for 4 hours.

PSA has been shown to form complexes with α2 macroglobulin (MG) and the serine protease inhibitor, antichymotrypsin (ACT). To explore its complex formation, hK2 was incubated with a series of common proteases present in human plasma (ACT, α2-antiplasmin, antithrombin III, and α1-antitrypsin (Travis and Salvesen, Ann. Rev. Biochem., 52, 655 (1983)) and the mixtures were analyzed by Western blot (FIG. 18). Any covalent complex of hK2 with these serpins should result in ~80–100 kD band on SDS/PAGE under reducing conditions.

ACT and α2-antiplasmin formed significant complexes with hK2 (FIG. 18, lane 1 and 2). Antithrombin III (lane 3) and α1-antitrypsin (α1 protease inhibitor, lane 4) formed no detectable complex with hK2. MG, a major component of blood plasma, also rapidly complexed with hK2 (lane 5). This complex corresponds to Mr of ~200 kD and 120 kD, which were also formed when PSA was incubated with purified MG (FIG. 18, lane 8, see below). It was particularly interesting that hK2 did not form complexes with α1-antitrypsin, even though this protein inhibits a wide range of trypsin-like proteases (Loebermann et al., J. Mol. Biol., 177, 531 (1984); Carrell and Travis, TIBS, 10, 20 (1985)).

It was not surprising that hK2 formed a complex with α2-antiplasmin since this protein has arginine residues in its inhibitor active site (Hunt and Dayhoff, Biochem. Biophy. Res. Comm., 95, 864 (1980); Chandra et al., Biochemistry, 22, 5055 (1983); Potempa, et al., Science, 241, 699 (1985); Shieh et al., J. Biol. Chem., 264, 13420 (1989); Mast et al., Biochemistry, 30, 1723 (1991)). However, it was also not expected that hK2 would form a complex with ACT, since ACT has a leucine in its inhibitor active site. Clearly the structural similarities between PSA and hK2 influence their complex formation with a common inhibitor even though their proteolytic specificity is entirely different as demonstrated in FIG. 16 and Table 2.

When spiked into human female serum hK2 formed a rapid complex with MG as detected by Western blot (FIG. 18). Lane 1 and lane 3 are hK2 and serum only controls, respectively. Lane 2 is hK2 incubated with ACT showing the 90 kD hK2-ACT complex and residual hK2. Lanes 4 and 5 are hK2 spiked into serum for 15 minutes and 1 hour, respectively. Lane 6 is hK2 incubated with purified MG for 4 hours. Lane 7 is PSA spiked into serum for 15 minutes and Lane 8 is PSA incubated with purified MG for 4 hours.

These results show that MG is the major complex when hK2 or PSA are spiked into human serum in in vitro experiments. Since PSA complex with ACT is known to occur in the blood serum of patients with prostate disease, it is likely that hK2 present in serum would also form some level of ACT complex.

Discussion

The in vivo protein processing and secretion mechanisms for PSA or hK2 are not known. The results presented herein show that phK2 is secreted by AV12-hK2, DU145-hK2, and PC3-hK2 cells, indicating that hK2 is normally secreted as phK2 and the propeptide is cleaved extracellularly. This suggests that phK2 exists in biological fluids and thus could be a useful diagnostic marker for pCa or BPH.

Both the mutant form of hK2 (hK2$^{v217}$) and the wild type form of hK2 were purified from AV12 cells. hK2 was very unstable to the purification procedures employed which, as found with other proteases, may be due to its autocatalytic property, and makes it very difficult to purify hK2 or phK2 in quantities sufficient for use as immunogens and calibrators. In contrast, phK2$^{v217}$ is highly stable and is converted to hK2$^{v217}$, which was also stable, by trypsin digestion. Purified phK2$^{v217}$ and hK2$^{v217}$ provided immunogens to generate mAbs specific for hK2 and phK2.

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed is:

1. An isolated, purified variant mature, pro- or variant pre-pro hK2 polypeptide having an amino acid substitution at a position in wild type mature hK2 polypeptide (SEQ ID NO:12) selected from the group consisting of position 183, position 206, position 217, position 189, position 96, position 41, position 205, position 204, position 187, and position 188, wherein the variant polypeptide binds antibodies which bind to hK2 but do not bind to hK3.

2. An immunogenic composition comprising the isolated variant hK2 polypeptide of claim 1 in combination with a pharmaceutically acceptable carrier, wherein the administration of the immunogenic composition to an animal induces the production of antibodies to said variant hK2 polypeptides.

* * * * *

UNITED STATES PATENT AND TRADEMARK OFFICE
CERTIFICATE OF CORRECTION

PATENT NO. : 6,103,237
DATED : August 15, 2000
INVENTOR(S) : Saedi et al.

It is certified that error appears in the above-identified patent and that said Letters Patent is hereby corrected as shown below:

<u>Title page,</u>
Item [75], delete ";Abhay Kumar; Kristine Kuus-Reichel, all" and insert -- , both --, therefor.

<u>Column 1,</u>
Line 7, before "incorporated"; delete "is" and insert -- are --, therefor.

<u>Column 6,</u>
Line 12, delete "10" and insert -- 10A --, therefor.
Line 23, delete "10" and insert -- 10B --, therefor.
Line 40, delete "12" and insert -- 12A --, therefor.
Line 50, delete "12" and insert -- 12B --, therefor.
Line 54, delete "13" and insert -- 13A --, therefor.
Line 66, delete "13" and insert -- 13B --, therefor.

<u>Column 7,</u>
Line 5, delete "14" and insert -- 14A --, therefor.
Line 17, delete "14" and insert -- 14B --, therefor.

<u>Column 19,</u>
Line 53, delete "resdues" and insert -- residues --, therefor.

<u>Column 20,</u>
Line 35, delete "residuse" and insert -- residues --, therefor.

<u>Column 22,</u>
Line 14, delete "residuse" and insert -- residues --, therefor.

UNITED STATES PATENT AND TRADEMARK OFFICE
CERTIFICATE OF CORRECTION

PATENT NO.    : 6,103,237
DATED         : August 15, 2000
INVENTOR(S)   : Saedi et al.

It is certified that error appears in the above-identified patent and that said Letters Patent is hereby corrected as shown below:

Column 25,
Line 19, delete "residuse" and insert -- residues --, therefor.

Signed and Sealed this

Eighth Day of July, 2003

JAMES E. ROGAN
*Director of the United States Patent and Trademark Office*